United States Patent [19]

Sato

[11] Patent Number: 5,049,681

[45] Date of Patent: Sep. 17, 1991

[54] OPTICALLY ACTIVE ALLYL ALCOHOL AND PROCESS FOR PRODUCING LEUCOTRIENE B4 USING THEREOF

[75] Inventor: Fumie Sato, Fujisawa, Japan

[73] Assignee: Nissan Chemical Industries, Ltd., Tokyo, Japan

[21] Appl. No.: 216,336

[22] Filed: Jul. 8, 1988

[30] Foreign Application Priority Data

Aug. 7, 1987 [JP] Japan ................................. 62-170299
Aug. 7, 1987 [JP] Japan ................................. 62-170300

[51] Int. Cl.$^5$ ...................... C07D 309/04; C07F 7/22; C07F 7/08; C07C 33/04
[52] U.S. Cl. .................... 549/206; 549/214; 549/415; 549/416; 549/420; 549/423; 556/87; 556/437; 556/443; 556/445; 560/179; 560/183; 560/205; 568/673; 568/675; 568/687; 568/845; 568/849; 568/855; 568/873
[58] Field of Search ............... 556/437, 87, 443, 445, 556/449; 568/845, 849, 673, 675, 687, 688-693, 855, 873; 560/179, 183, 205; 549/206, 214, 415, 416, 420, 423

[56] References Cited

U.S. PATENT DOCUMENTS 3,962,351  6/1976  Sih ........................................ 568/849
4,151,187  4/1979  Collins et al. ........................ 549/206
4,233,231  11/1980  Floyd et al. .......................... 556/87

FOREIGN PATENT DOCUMENTS 0255379  3/1988  European Pat. Off. .

OTHER PUBLICATIONS

Sato et al., Tetrahedron Letters, vol. 28, No. 447, pp. 5849-5852, 1987.
Rao et al., J. Organic Chem 51(22) 4158-4159, 1986.
Journal of the American Chemical Society, vol. 106, No. 19, 9/19/84, pp. 5734-5736, K. C. Nicolaou et al., "Total Synthesis of 5(S), 15(S)-Dihydroxy-6, 13-trans-8, 11-cis-eicosatetraenoic acid . . .".
Tetrahedron Letters, vol. 27, No. 48, 1986, pp. 5853-5856, P. Pianetti et al., "Optically active propargylic alcohols from D-xylose useful precursors for LTB4 synthesis".
Tetrahedron Letters, vol. 28, No. 18, 1987, pp. 2033-2036, Express Litho Service, Oxford, GB, S. Okamoto et al., "A highly efficient synthesis of gamma-halo allylic alcohols & propargylic alcohols with high optical purity. Practical method for synthesis of the prostaglandin omega-chain".
Synthesis, No. 6, 6/86, pp. 453-461, K. C. Nicolaou et al., "Stereocontrolled Total Synthesis of Lipoxins B".
Synthesis, No. 4, 4/86, pp. 344-347; K. C. Nicolaou et al., "A General Strategy for the Synthesis of Monohydroxyeicosatetraenoic Acids: Total Synthesis of 5(S)-Hydroxy-6(E),8,11,14(Z)-eicosatetraenoic Acid (5-HETE) & 12(S)-Hydroxy-5-8-14(Z),10(E)-eicosatetraenoic Acid (12-HETE)".
Tetrahedron Letters, vol. 26, No. 22, 1985, pp. 2679-2682, S. Hashimoto et al., "Synthesis of clavulones(claviridenones)".
Journal of the American Chemical Society, vol. 108, No. 18, 9/3/96, pp. 5644-5646, H. Jin et al., "Catalytic Effect of Nickel(II) Chloride & Palladium(II) Acetate on Chromium(II)-Mediated Coupling Reaction of Iodo Olefins with Aldehydes".
Chemical Abstracts, vol. 104, 1986, p. 503, Abstract No. 50702s, Columbus, Ohio, U.S., T. Tanaka et al., "Prostaglandin Chemistry, Part XXIV, Synthesis of 7-thiaprostaglandin E1 congeners; potent inhibitors of platelet aggregation", & Chem. Parhm. Bull. 1985, 33(6), 2359-2385, Abstract Chem. Abstr., Chem. Subst., 11th Coll. Index, vol. 96-105, p. 47646CS: 1-Penten-3-ol, 5-ethoyx-1-iodo-, benzoate . . .

(List continued on next page.)

Primary Examiner—Gary P. Straub
Assistant Examiner—Stuart L. Hendrickson
Attorney, Agent, or Firm—Birch, Stewart, Kolasch & Birch

[57] ABSTRACT

A novel optically active allyl alcohol derivative represented by the following general formulae (I), (II), (III) and (IV):

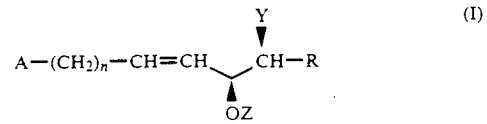

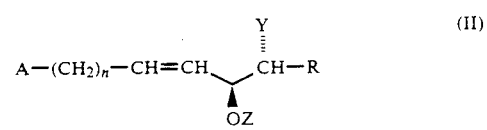

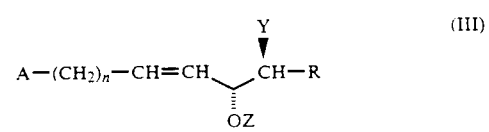

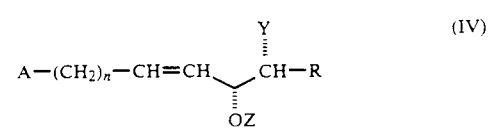

The novel optically active allyl alcohol can be used effectively for producing leucotrienes B4 by the process of reacting an optically active halogen substituted allyl alcohol and a novel optically active acetylene-substituted allyl alcohol.

3 Claims, No Drawings

OTHER PUBLICATIONS

Tetrahedron Letters, vol. 22, No. 35, 1981, pp. 3339–3342, Pergamon Press, Oxford, GB, E. J. Corey et al.: "Total Synthesis of 5S,12S-dihydroxy-6,10-E,8,-14-Z-eicosatetraenoic acid (5S,12S-di-HETE) (2), a new human metabolite of arachidonic acid".

Tetrahedron Letters, vol. 26, No. 11, 1985, pp. 1399–1402, Pergamon Press, Oxford, GB, Y. LeBlanc et al.: "Total synthesis of lipoxin B: assignment of stereochemistry".

Chemical Abstracts, vol. 103, 1985, p. 703, Abstract No. 123239n, Columbus, Ohio, U.S., M. Dorta de Marquez et al.: "Natural acetylenes. Part 60, Synthesis of C22 and C23 diacetylenes, constituents of the sponge Reniera fulva", & J. Chem. Res. Synop. 1985, (4), 104–105, Chemical Abstracts, Chemical Substances, Eleventh Collective Index, vols. 96–105, p. 24710CS: 1-13--Eicosadien-3-ol,1-(trimethylsilyl)-[R-(?,Z)], RN 98119-66-5.

Chemical Abstracts, vol. 103, 1985, p. 698, Abstract No. 141711q, Columbus, Ohio, U.S.; K. Green et al.: "Natural acetylenes, Part 59. Synthesis of (−)-(E,S-)-dodec-4-ene-6,8,10-triyn-3-ol, the enantiomer of a metabolite of the fungus Peniophora resinose Jackson & Dearden", & J. Chem. Res., Synop. 1985, (4), 103, Chemical Abstracts, Chemical Substances, Eleventh Collective Index, vols. 96–105, p. 3188rCS: 4-Hepten-6-yn-3-ol, [S-(E)]-RN 98329-78-3, 4-Hepten-6-yn-3-ol, 7-(trimethylsilyl)-[S-(E)], RN 98329-77-2.

Tetrahedron Letters, vol. 28, No. 47, 1987, pp. 5849–5852, Express Litho Service, Oxford, GB; Y. Kobayashi et al., "Highly stereocontrolled, multigram scale synthesis of leukotriene B4".

Tetrahedron Letters, vol. 28, No. 50, 1987, pp. 6351–6354, Express Litho Service, Oxford, GB, Y. Kitano et al., "A highly efficient synthesis of optically pure gamma-iodo allylic alcohols and their conversion into various optically active allylic alcohols".

Chemical Abstracts, vol. 107, 1987, p. 745, Abstract No. 236269y, Columbus, Ohio, U.S., K. C. Nicolaou et al., "Stereocontrolled total synthesis of lipoxin A5 and B5", & Angew. Chem. 1987, 99(10), 1077–1079, Chemical Abstracts, Chemical Substance Index, vol. 107, p. 4252CS: 6-Heptenoic acid, 7-bromo-5[[(1,1-dimethylethyl)diphenylsilyl]oxy],methyl ester, [S(E)]-RN 110569-23-8, p. 8463CS, Silane, (1,1-dimethylethyl)[[1-(2-iodoethenyl)-3-hexenyl]oxy] dimethyl-, [S--(E,Z)]-RN 110569-09-0.

Tetrahedron, vol. 44, No. 13, 1988, pp. 4074–4086, Pergamon Press, Oxford, GB, Y. Kitano et al., "A highly efficient kinetic resolution of gamma- and beta-trimethylsilyl secondary allylic alcohols by the sharpless asymmetric epoxidation".

Chemical Abstracts, vol. 111, 1989, p. 682, Abstract No. 153432c, Columbus, Ohio, U.S., Y. Kabayashi et al., "Enantio- and stereoselective total synthesis of leukotriene B4, 5(S)-HETE, and 12(S)-HETE", & Tennen Yuki Kagobutsu Toronkai Koen Yoshishu 1988, 30, 580–587.

OPTICALLY ACTIVE ALLYL ALCOHOL AND PROCESS FOR PRODUCING LEUCOTRIENE B4 USING THEREOF

BACKGROUND OF THE INVENTION

FIELD OF THE INVENTION

The present invention relates to a novel allyl alcohol derivative which is useful as an intermediate for the synthesis of physiologically active compounds having strong physiological activity such as leucotriene B4 (LTB4), lipoxine, hydroxyeicosatetraene (HETE), etc., the present invention further relates to a process for producing these leucotrienes B4.

Physiologically active compounds such as leucotriene B4, etc., have been noted so far and various processes have been proposed for synthesizing these compounds. Particularly, it has been known that leucotrienes have strong physiological activity and, for example, leucotriene B4 has strong leukocyte attracting effect. In view of the above, although there have been proposed various synthesis processes for the leucotrienes, these conventional synthesis processes involve many problems.

For example, while various processes for synthesizing leucotriene B4 have been known, most of these are methods which comprises complicated steps using optically active intermediates derived from saccharides. While on the other hand, the following methods have been known as the process which do not use saccharide-derived optically active intermediates.

(1) A method of using an optically active ynol derivative obtained by subjecting an ynone derivative to asymmetric hydrogen reduction using an optically active hydrogenated boron reagent as the starting material (Nicolaou, et al., J. Amer. Chem. Soc. 106, 3548 (1984))

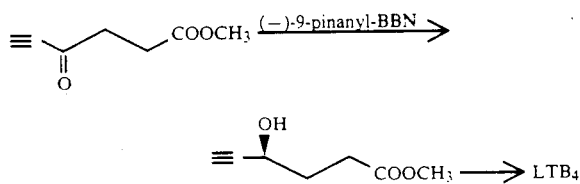

(2) A method using an optically active α-oxyaldehyde obtained by utilizing enzymatic asymmetric reduction or asymmetric hydrolysis (C. J. Sih, et al., J. Org. Chem., 51, 1253 (1986))

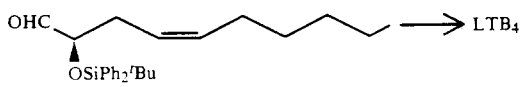

However, any of the processes (1) or (2) above is not practical as the process for producing leucotriene at a high purity and in a great amount, because it requires expensive asymmetric reducing agent and it is poor in the yield and the selectivity in the asymmetric reaction.

SUMMARY OF THE INVENTION

Accordingly, it is an object of the present invention to provide an allyl alcohol derivative as a novel intermediate capable of advantageously synthesizing a physiologically active compound such as leucotriene.

Further, another object of the present invention is to provide a process capable of advantageously synthesizing leucotriene B4 or derivatives thereof.

The present inventors have made an earnest study for various allyl alcohol derivatives and, as a result, have found that a novel allyl alcohol derivative represented by the following general formulae (I)–(IV).

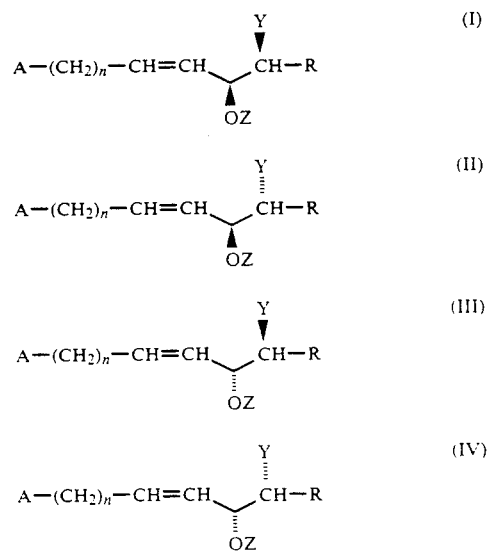

where A represents $R^1R^2R^2Sn$, $R^1R^2R^2Si$ halogen atom, $-C\equiv CH$ or $-C\equiv CSiR^1R^2R^3$, in which $R^1$, $R^2$ and $R^3$ represent respectively alkyl group with 1 to 5 carbon atoms, Y represents H or OZ', Z and Z' represent respectively H or protection group for hydroxyl group, R represents an alkyl group with 1 to 10 carbon atoms, alkoxy carbonyl group substituted alkyl group with 1 to 10 carbon atoms, bis(alkoxy)methyl group-substituted alkyl group with 1 to 10 carbon atoms, carboxyl group-substituted alkyl groups with 1 to 10 carbon atoms, alkenyl group with 1 to 10 carbon atoms, alkoxy carbonyl group-substituted alkenyl group 1 to 10 carbon atoms, carboxyl group alkenyl group substituted with 1 to 10 carbon atoms, bis(alkoxy)methyl group-substituted alkenyl group with 1 to 10 carbon atoms, alkynyl group with 1 to 10 carbon atoms, alkoxy carbonyl group-substituted alkynyl group with 1 to 10 carbon atoms, carboxyl group-substituted alkynyl group with 1 to 10 carbon atoms, or bis(alkoxy)methyl group-substituted alkynyl group with 1 to 10 carbon atoms, providing that A is not $R^1R^2R^3Sn$, $R^1R^2R^2Si$ or halogen atom in a case if R is an alkyl group with 1 to 10 carbon atoms, and n is 0 or 1 can be obtained according to the reaction schemes a - t described later, these allyl alcohol derivatives are useful as the intermediate for the synthesis of physiologically active compounds such as leucotriene B4 and the physiologically active compound such as leucotriene B4 can be synthesized at high yield by way of these allyl alcohol derivatives.

The novel allyl alcohol derivatives include the following novel optically active trans-halogen substituted allyl alcohol derivatives having the general formulae (V) and (VI) and the following novel optically active cisacetylene substituted allyl alcohol derivatives.

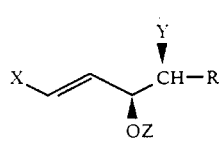
[V]

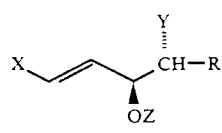
[VII]

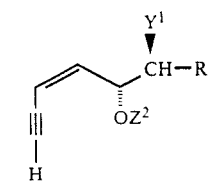
[VII]

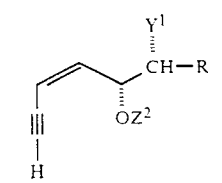
[VIII]

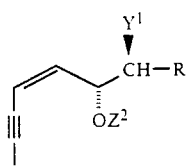
[VII]

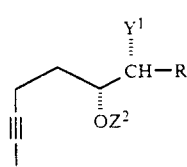
[VIII]

where X represents halogen atom, $Z^2$ represents H or protection group for hydroxyl group and $Z^3$ represents protection group for hydroxyl group, and Y Z and R have the same meaning as described above.

Furthermore, we have also found that leucotrienes $B_4$ can be obtained by using the novel allyl alcohol derivatives as follow:

The leucotrienes $B_4$ and the derivatives thereof represented by the general formula (IX):

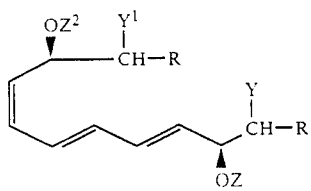
[IX]

by reacting the optically active tran-halogen-substituted allyl alcohol derivative of the formula (V) or (VI):

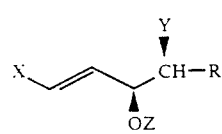
[V]

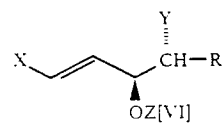
[VI]

and the optically active cis-acetylene-substituted allyl alcohol derivative of the formula (VII) or (VIII):

Particularly, the leucotrienes $B_4$ and the derivatives thereof represented by the following general formula XIV:

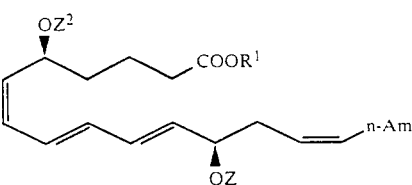
[XIV]

where Z represents a hydrogen atom, a protection group for hydroxyl group, $Z^2$ represents as hydrogen atom or protection group for hydroxy group, R' represents an alkyl group with 1 to 5 carbon atoms and n-Am represents an n-amyl group, can be synthesized at a high yield with an industrial advantage, by reacting a novel optically active halogen-substituted allyl alcohol represented by the following general formula (XV):

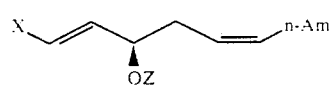
[XV]

(where X represents a hydrogen atom and Z and n-Am have the same meanings as described above) with a novel optically active acetylene-substituted allyl alcohol of the following general formula (XVI):

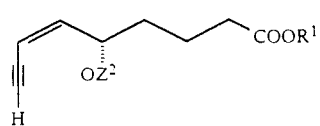
[XVI]

where R' and $Z^2$ have the same meanings as described above.

DETAILED DESCRIPTION OF THE INVENTION

The novel allyl alcohol derivative according to the present invention is shown by the formulae (1)–(IV) including the formula (V)–(VIII) described above.

In the formulae (I)–(VIII), alkoxy group can include methoxy, ethoxy, propoxy, butoxy, etc., bis(alkoxy) group can include

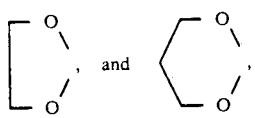

and protection group for the hydroxyl group represented by A, $Z^1$, $Z^2$ or $Z^3$ can include trialkylsilyl group, for example, trimethylsilyl group, t-butyldimethylsilyl group and phenyldimethylsilyl group, alkoxyalkyl group, for example, methoxymethyl group, ethoxyethyl group, tetrahydropyranyl group, aralkyl oxyalkyl group, for example, benzyloxymethyl group, trityl group and, acyl group, for example, acetyl group, p-nitrobenzoyl group, 2,4-dinitrophenylcarbonyl a group, etc.

Specific examples for R can include: $R^4OOC(CH_2)_x-$, $CH_3(CH_2)_yCH=CH-$,

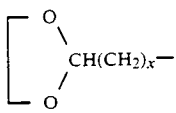

$R^5OOC(CH_2)_z(CH=CH-$ where $R^4$ and $R^5$ respectively represent hydrogen or alkyl group with 1 to 5 carbon atoms, x is an integer of 1 to 10, y is an integer of 1 to 7 and z is an integer of 1 to 8.

Among the allyl alcohol derivatives as described above, the compound in which the substitutes A is $R^1R^2R^3Sn$ can be synthesized, for example, in accordance with the following reaction schemes a–d:

Reaction scheme a

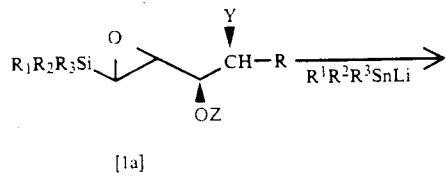

[1a]

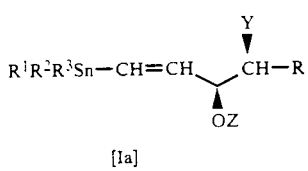

[Ia]

Reaction scheme b

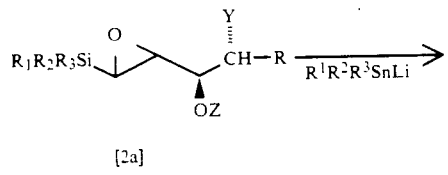

[2a]

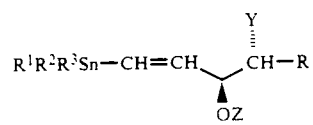

[IIa]

Reaction scheme c

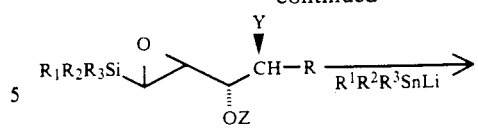

[3a]

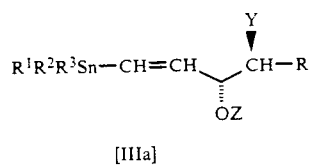

[IIIa]

Reaction scheme d

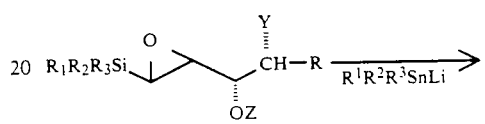

[4a]

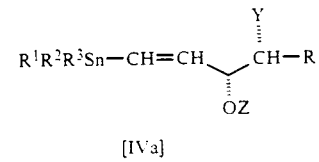

[IVa]

where $R_1$, $R_2$, $R_3$ represent respectively alkyl group with 1 to 5 carbon atoms According to the syntheses of the reaction schemes a–d, trans type compounds can be synthesized in all of the cases. In this case, as the conditions for the synthesis process, it is preferred to use the compounds (1a)–(4a) $R^1R^2R^3SnLi$ upon reaction such that the compound of $R^1R^2R^3SnLi$ is used in a slight excess molar amount relative (1 to 1.4 times) to the compounds (1a)–(4a). Although there is no particular restriction for the reaction temperature, it is preferred to conduct the reaction at $-40°$ C.– $80°$ C. and the reaction is completed usually in 1–5 hours at room temperature. As the reaction solvent, those solvents having no direct concern with the reaction, for example, ether type solvent such as diethyl ether, tetrahydrofuran or dimethoxyethanes if necessary, incorporated with hexane, hexamethylphosphortriamide or dimethylsulfoxide can be used. In a case where the thus obtained compound has a protection group for the hydroxyl group or the protection group for the carboxyl group (group represented by Z, $Z^1$, $Z^2$, $Z^3$, $R^4$, $R^5$ described above), it is possible to react the protection group as described above and then convert into hydrogen atom by way of decapping or hydrolysis. On the contrary, the hydroxyl group or carboxyl group may be protected or esterified.

The following reaction scheme is also possible for obtaining the compounds (IVa).

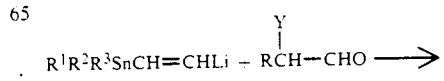

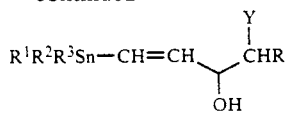

[IVa]

Then, a compound in which the substituent A is halogen can be synthesized from the compound ((Ia)–(IVa) in which the substituent A is $R^1R^2R^3Sn$ in accordance with the following reaction schemes e–h.

Reaction scheme e

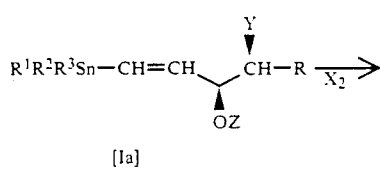

[Ia]

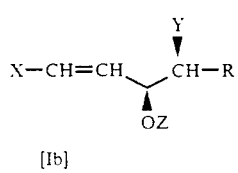

[Ib]

Reaction scheme f

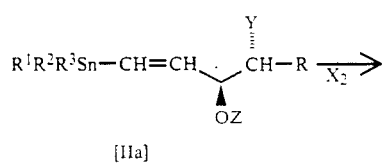

[IIa]

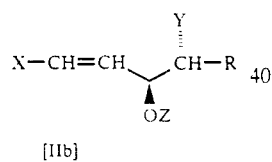

[IIb]

Reaction scheme g

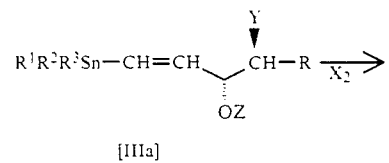

[IIIa]

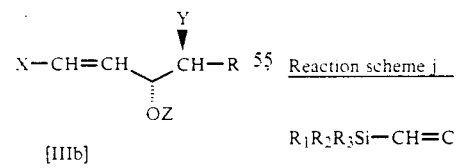

[IIIb]

Reaction scheme h

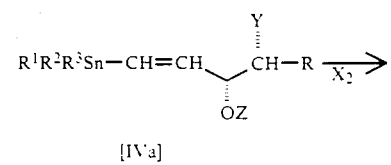

[IVa]

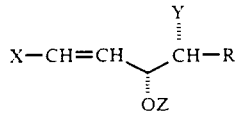

[IVb]

According to the syntheses of the reaction schemes e–h, it is possible to synthesize a trans-form from a trans-compound and a cis-form from cis-compound.

In these synthesis process it is preferred, as the reaction conditions, to use halogen molecules in a slight excess molar amount (1 to 1.4 times) upon reacting the compound (Ia)–(IVa) with halogen molecule ($X_2$). The reaction is preferably carried to at a reaction temperature of from $-80°$ C. to $40°$ C. and the reaction is completed usually by from 0.1 to 2 hours at a temperature from $-20°$ C. to $20°$ C. As the reaction solvent, those not directly concerned with the reaction and those of lower boiling point in view of the easy work-up of the reaction are preferably used and they can include, for example, ether type solvent such as diethyl ether or dimethyl ether, halogenated type solvent such as methylenechloride or dichloroethane and aromatic solvent such as benzene.

In the case of the compound having the protection group for hydroxyl group or the protection group for carboxyl group, the group can be converted as described above into H by decapping or hydrolysis after the reaction described above. While on the other hand, the hydroxyl group or carboxyl group may be protected or esterified.

The compound in which the substituent A is halogen can be synthesized as shown by the following formulae.

Reaction scheme i

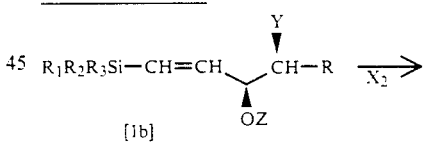

[Ib]

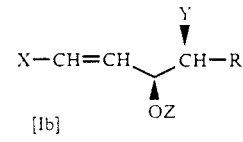

[Ib]

Reaction scheme j

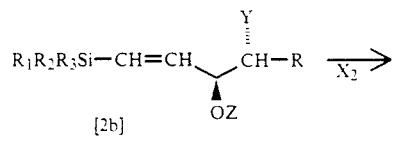

[2b]

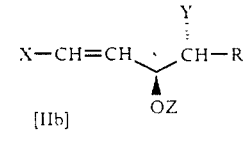

[IIb]

Reaction scheme k

-continued

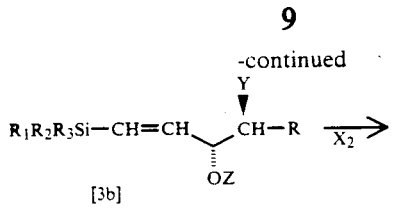
[3b]

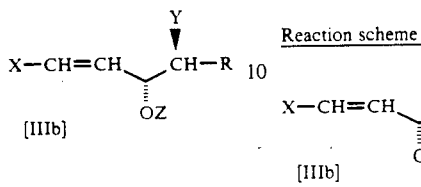
[IIIb]

Reaction scheme l

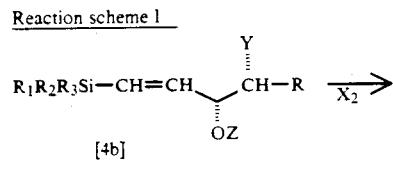
[4b]

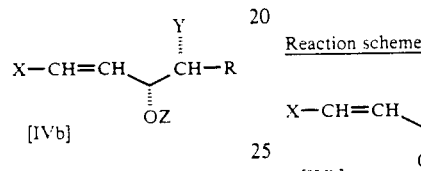
[IVb]

According to this synthesis process, it is possible to synthesize a cis-form from a cis-compound and a trans-form from cis-compound.

In these synthesis processes, it is preferred as the reaction conditions, to use halogen molecules in a slight excess molar amount (1 to 1.4 times) upon reacting the compounds (Ib)-(IVb) with halogen molecule ($X_2$). The reaction is preferably carried out at a reaction temperature of from $-80°$ C. to $40°$ C. and the reaction is completed usually by from 0.1 to 2 hours at a temperature from $-20°$ C. to $20°$ C. As the reaction solvents those solvents not directly concerned with the reaction and those solvents of lower boiling point in view of the easy work-up of the reaction are preferably used and they can include, for example, ether type solvent such as diethyl ether or dimethyl ether, halogenated type solvent such as methylenechloride or dichloroethane and aromatic solvent such as benzene.

Further, the compound in which the substituent group is $R^1R^2R^3Si-C\{C-$ can be synthesized, for example, in accordance with the reaction schemes m-p from the compound in which the substituent A is X by using trialkylsilyl acetylene ($R^1R^2R^3Si-C\equiv C-$).

Reaction scheme m

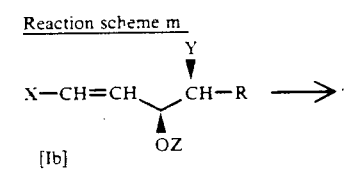
[Ib]

-continued

R¹R²R³Si—C≡C—CH=CH CH—R
                        |
                       OZ
[IIc]

Reaction scheme o

X—CH=CH CH—R ⟶
              |
             OZ
[IIIb]

R¹R²R³Si—C≡C—CH=CH CH—R
                      |
                     OZ
[IIIc]

Reaction scheme p

X—CH=CH CH—R ⟶
              |
             OZ
[IVb]

R¹R²R³Si—C≡C—CH=CH CH—R
                      |
                     OZ
[IVc]

According to this synthesis process, it is possible synthesize a trans-form from a trans-compound and a cis-form from a cis-compound.

In these synthesis processes, it is desirable to use trialkylsilyl acetylene in a slight excess molar amount (1 to 1.4 times) upon reacting the compounds (Ic)-(IVc) with trialkylsilyl acetylen ($R^1R^2R^3SiC\equiv CH$) to use a slight excess molar amount of trialkylsilyl acetylene. The reaction temperature is suitably from $-80°$ C. to $40°$ C., and the reaction is usually completed in 0.1 to 100 hours at a temperature from $-20°$ C. to $20°$ C. For the reaction solvent, an aromatic solvent such as benzene can be used.

The protection group for hydroxyl group, the protection group for carboxyl group and the processing for hydroxy group or carboxy group are the same as described above.

Furthermore, the compound in which the substituent is $-C\equiv CH$ can be prepared from the compounds (Ic)-(Vc) as described above in which the substituent A is $R^1R^2R^3Si-C\equiv C-$ in accordance with the following schemes.

Reaction scheme q

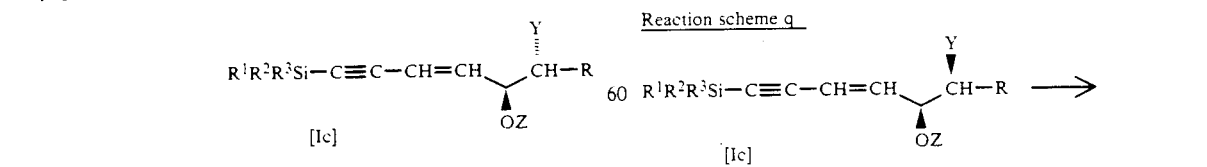
[Ic]

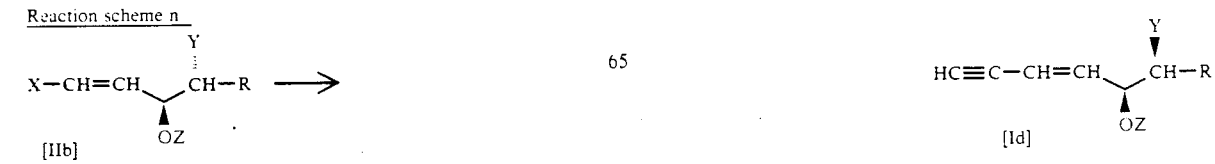
[Id]

Reaction scheme n

X—CH=CH CH—R ⟶
              |
             OZ
[IIb]

Reaction scheme r

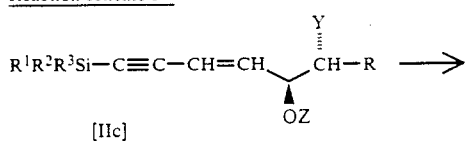

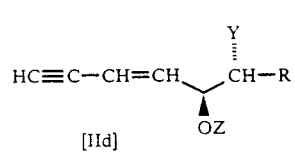

Reaction scheme s

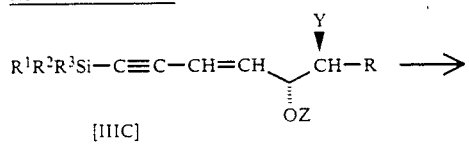

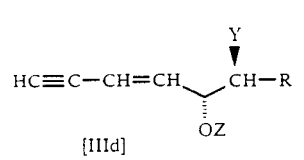

Reaction scheme t

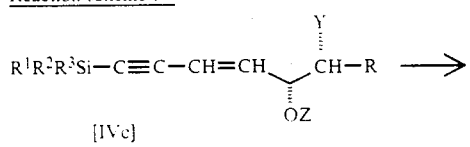

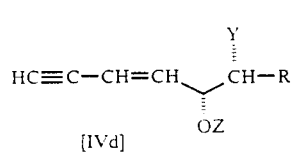

According to this synthesizing process, it is possible to synthesize a trans-form from a trans-compound, and a cis-form from a cis-compound.

In these synthesizing processes, conditions for the desilylation of —C—SiR$^1$R$^2$R3 group of the compounds (Ic)–(IVc) are generally used as the reaction conditions. Depending on the type of the protection group of Z, Z$^1$, Z$^2$ and Z$^3$, however, there may be selected such a process as not affecting them or, on the contrary, a method of decapping them simultaneously depending on the case. As an instance, the compounds (Id)–(IVd) can be obtained with no effect on Z, Z$^1$, Z$^2$ or Z$^3$ by preparing a solution of the compounds (Ic)–(IVc) in a solution of tetrahydrofuran: ethanol: water = 1:1:1 ratio, adding silver nitrate and then potassium cyanate at 0° C., followed by stirring.

It should be noted that the compound in which the substituents A is R$^1$R$^2$R$^3$Si can be synthesized, for example, in accordance with the following reaction schemes u and v.

Reaction scheme u

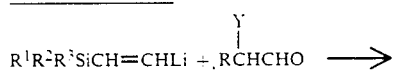

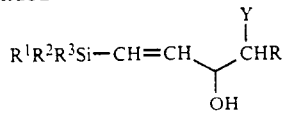

Reaction scheme v

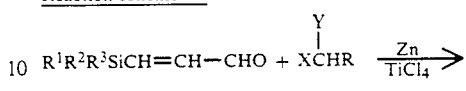

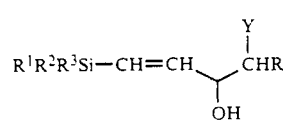

The allyl alcohol derivative according to the present invention is useful as an intermediate for synthesizing physiologically active substances such as leucotriene B$_4$, lipoxine and HETE and these physiologically active substances can be synthesized at high yield by way of these allyl alcohol derivatives.

Referring more specifically to the production process for the leucotriene B$_4$ or the derivative thereof, the optically active halogen-substituted allyl alcohols and an optically active acetylene-substituted allyl alcohols are brought into reaction, as described above according to the following equations.

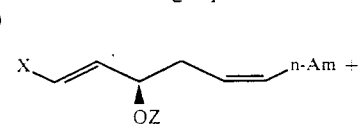

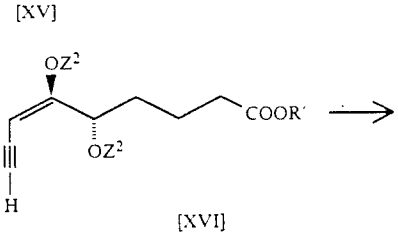

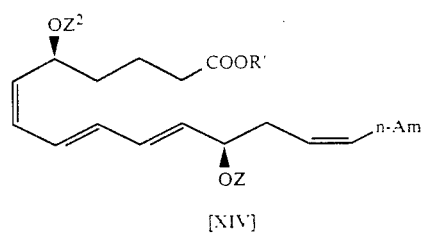

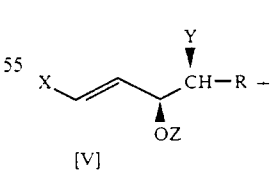

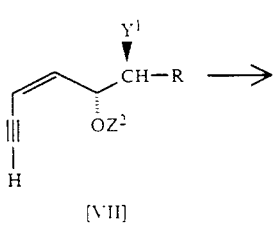

-continued

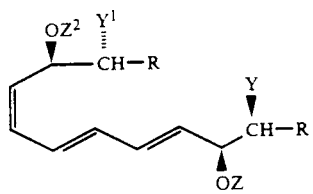
[X]

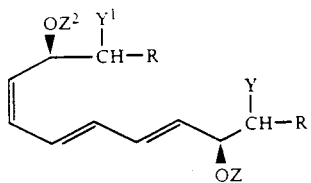
[V]

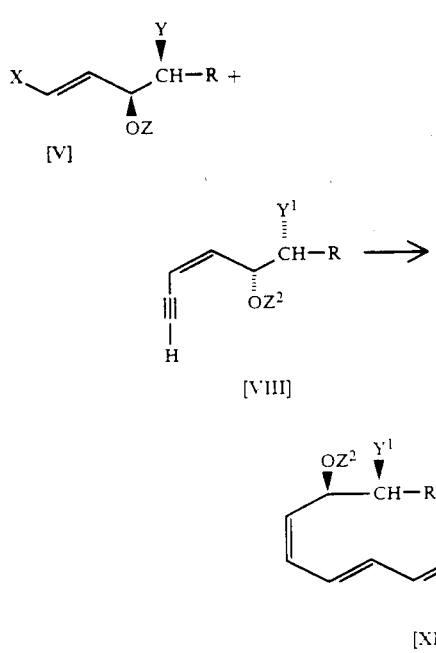
[VIII]

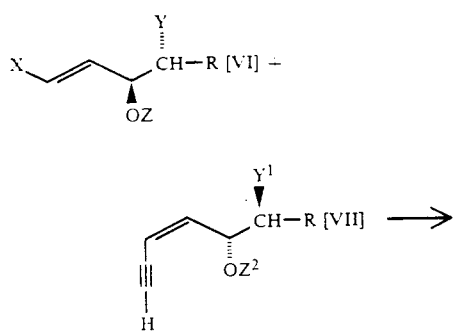
[XI]

It should be noted that the above formulae (X) to (XIII) are described collectively to the following formula (IX).

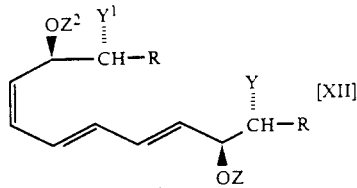 [IX]

The particular equation is as follows:

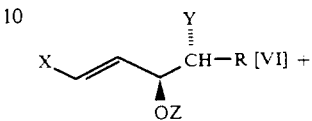

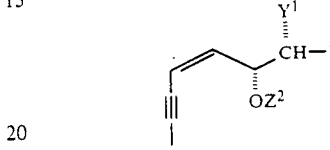

-continued

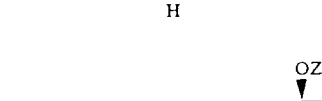
[XII]

[VI] +

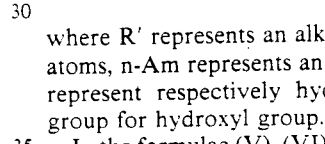
[VIII] →

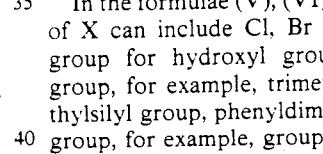
[XIII]

where R' represents an alkyl group with 1 to 5 carbon atoms, n-Am represents an n-amyl group and Z and $Z^2$ represent respectively hydrogen atom or protection group for hydroxyl group.

In the formulae (V), (VI), and (XV) the halogen atom of X can include Cl, Br and I, while the protection group for hydroxyl group can include trialkylsilyl group, for example, trimethylsilyl group, t-butyldimethylsilyl group, phenyldimethylsilyl group, alkoxyalkyl group, for example, group, aralkyl oxyalkyl group, for example, benzyloxymethyl group, trityl group or acyl group, for example, acetyl group or p-nitrobenzoyl group.

For the reaction of the compound of the general formula (V), (VI) or (XV) and the compound of the general formula (VII), (VIII) or (XVI) preferred conditions are such that hydroborane is acted on the compound (VII), (VIII) or (XVI) which is then brought into reaction with the compound (V),(VI) or (XV) under the presence of two or greater molar amount of a base and a palladium catalyst.

The hydroborane can include, for example, disiamylborane (HB(—CHCHMe₂)₂), 1,3,2-benzodioxaboronol
              |
              Me

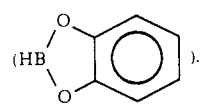

The palladium catalyst can include, for example, tetrakis(triphenylphosphine)palladium, bis(triphenylphosphine) palladium dichloride and palladium diacetate. The base can include, for example, an aqueous solution of sodium hydroxide, alcohol solution of sodium alkoxide, potassium acetate, etc. Ether type solvent such as tetrahydrofuran or aromatic solvent such as benzene can suitably be used as the solvent.

In this case, the reaction temperature is preferably from −80° C. to 40° C. The reaction time is usually from 0.1 to 10 hours.

In the compound of general formulae (IX) ((X), (XI), (XII), (XIII)) and (XIV) obtained in accordance with the above-mentioned process, decapping of the protection group for hydroxyl group and the protection for hydroxyl group can be conducted by the customary method. Further, known method can be employed also for the purification method, etc.

Furthermore, the compound represented by the general formula (XV) or (XVI) described above can be produced in accordance with the following reaction schemes according to the reaction schemes a-t described above.

Synthesis for the compound of general formula (XV)

$$R_1R_2R_3Si\underset{OZ}{\overset{}{\diagdown}}\diagup\diagdown\diagup n\text{-Am} \xrightarrow{R^1R^2R^3SnLi} [XV]$$

$$R^1R^2R^3Sn\underset{OZ}{\overset{}{\diagdown}}\diagup\diagdown\diagup n\text{-Am} \xrightarrow{X_2}$$

$$X\underset{OZ}{\overset{}{\diagdown}}\diagup\diagdown\diagup n\text{-Am}$$

where $R_1$, $R_2$, $R_3$ represent respectively alkyl groups with 1 to 5 carbon atoms and Z and X have the same meanings as described above.

$$R_1R_2R_3Si\underset{OZ}{\overset{}{\diagdown}}\diagup\diagdown\diagup n\text{-Am} \xrightarrow{X_2} [XV]$$

$$X\underset{OZ}{\overset{}{\diagdown}}\diagup\diagdown\diagup n\text{-Am}$$

Synthesis for the compound of general formula (XVI)

$$X\underset{OZ^2}{\overset{}{\diagdown}}\diagup\diagdown\diagup n\text{-Am} \xrightarrow{R^1R^2R^3SiC\equiv CH} [XVI]$$

Where the typical process for synthesizing leucotriene B₄ is as shown by the following reaction scheme:

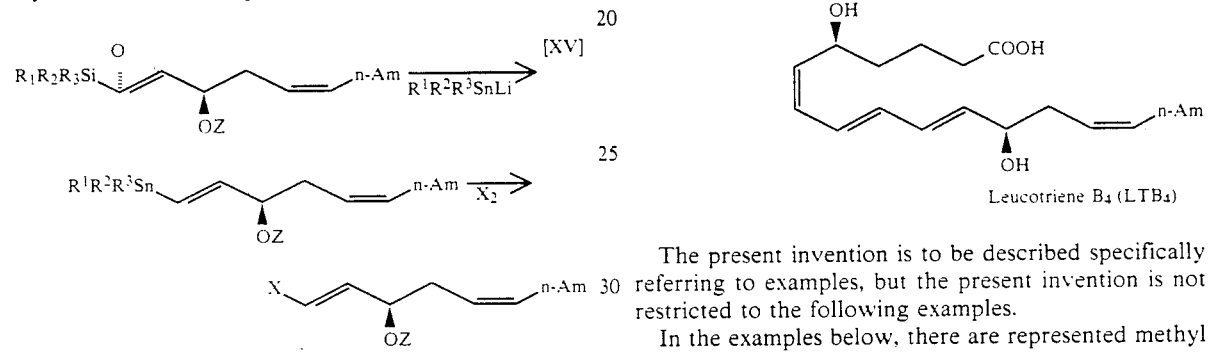

The present invention is to be described specifically referring to examples, but the present invention is not restricted to the following examples.

In the examples below, there are represented methyl group by Me, ethyl group by Et, propyl group by Pr, butyl group by Bu, amyl group by Am and phenyl by Ph.

EXAMPLE 1

Under an argon atmosphere, a solution of 6.2 g (16 mmol) of (E)-1-tri-n-butyl tin-t-trimethylsilylethylene in THF (25 ml) was cooled to -78.C, to which n-BuLi (10 ml, 15.3 mmol) in n-hexane was dropped and stirred for one hour to prepare compound (2).

On the other hand, a solution of the compound (1) (7.0 g, 54 mmol) in THF (30 ml) was cooled to −78° C. A solution of the compound (2) (54 mmol) in THF-n-hexane was dropped to the above-mentioned solution. After mixing at −78° C. for 30 min, the aqueous layer was extracted with benzene. The collected benzene solution was dried over MgSO₄ and concentrated under a reduced pressure. When crude product was purified on silica gel column chromatography (n-hexane : Et₂O=30:1 −3:1), 6.92 g (55.9 % yield) of the compound (3) was obtained.

Physical Property of the Compound (3)

IR (neat): 3400, 1727, 842 cm⁻¹.

¹H-NMR (CCl₄)δ: 5.97 (dd, J=18.3, 3.6Hz, 1H), 5.77 (d, J=18.3Hz, 1H), 4.08–3.86 (m, 1H), 3.58 (S, 3H), 3.02

(brS, 1H), 2.26 (t, J=7Hz, 2H) 2.05-1.25 (m, 4H), 0.07 (S, 9H)

13C-NMR (CDCl3)δ: 174.0, 148.3, 129.4, 74.0, 51.4, 36.2, 33.8, 20.8,-1.4.

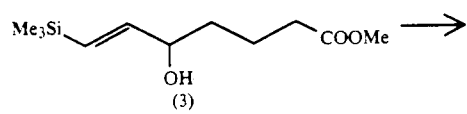

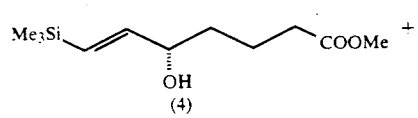

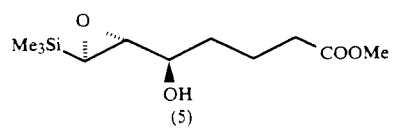

Using the compound (3) (4.0 g, 17.4 mmol), Ti(O-iPr)4 (5.18 ml, 17.4 mmol), D(−) diisopropyl tartarate (4.43 ml, 20.9 mmol), t-butylhydroperoxide (3.78 mol, in 6.9 ml CH2Cl2, 26.1 mmol) and CH2Cl2 (120 ml), the same procedures as the asymmetric epoxidization were conducted (−21° C., 20 h; work-up : Me2S (2.6 ml, 34.8 mmol), to obtain 10% tartaric acid (−8 ml), Et2O (120 ml), NaF (30 g)), 1.71 g (42.8 %) of the compound (4) and 1.93 g (45.1%) of the epoxide (5).

Physical Property of the Compound (4)

[α]25C+6.78° (C 1.15, CHCl3).

1H-NMR and IR are the same as those for the compound (3).

Physical Property of the Compound (5)

IR (neat): 3410, 1726, 1248, 843 cm−1

1H-NMR (CDCl3)δ: −0.08 (S, 9H), 1.2-1.8 (m, 4H), 2.08-2.29 (m,3H), 2.62 (t, J=5.1Hz, 1H), 2.82 (br d, J=2.4Hz, 1H), 3.46 (S, 3H), 3.40-3.62 (m, 1H).

13C-NMR (CDCl3)δ: 173.4, 69.5, 58.1, 50.9, 47.5, 33.6, 33.0, 20.5,-4.1.

[α]25D+6.74° (c=1.75, CHCl3).

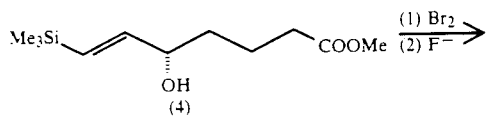

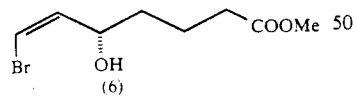

Bromine (0.39 ml, 7.5 mmol) was dropped to a solution compound (4) (1.71 g, 7.43 mmol) in CH2Cl2 (30 ml) cooled to 0° C. After 10 minutes, it was confirmed by TLC that the compound (4) was completely consumed. The solution was poured into a mixed solution of an aqueous solution of Na2S2O3 and an aqueous saturated solution of NaHCO3. The product was extracted twice with n-hexane. The hexane layer was dried over MgSO4 and then concentrated to obtain a bromine addition product.

The coarse product obtained as above was dissolved in THF (15 ml) and cooled to 0° C. n-Bu4NF (14 ml, 8.8 mmol, 0.63 mol in THF) was dropped to the solution and stirred for 10 minutes. After confirming the elimination of the starting material, it was poured into an aqueous saturated solution of NaCl. The product was extracted three times with ether. The collected organic layer was dried over MgSO4 and then concentrated to obtain 1.7 g (yield 100%) of the compound (6). The compound was used with no further purification to the next reaction. When purified on silica gel chromatography, the following data were obtained.

Physical Property of the Compound (6)

1H-NMR (CCl4)δ: 1.23-1.88 (m, 7H), 2.17-2.38 (m, 2H), 3.56 (S, 3H), 4.37-4.61 (m, 1H), 5.82-6.38 (m, 2H).

EXAMPLE 2

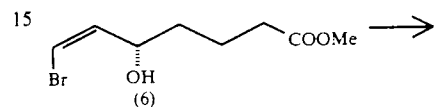

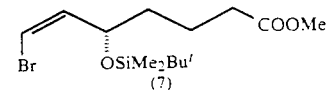

The compound (6) (1.7 g) was dissolved into DMF (20 ml) and cooled to 0.C. Imidazole (1.52 g, 22.3 mmol) and t-butyldimethyl chlorosilane (hereinafter simply referred to as TBSCl) (1.68 g, 11.1 mmol) were added to the solution and stirred at room temperature over one night.

The DMF solution was poured into an aqueous saturated solution, of NaHCO3 and the product was extracted three times with n-hexane. The hexane layer was dried over MgSO4 and then concentrated to obtain a crude product of the compound (7). When purifying on silica gel column chromatography, 1.92 g of the compound (7) (yield from the compound (4): 73.6%) was obtained.

Physical Property for the Compound (7)

IR (neat): 1737, 1249, 1088, 836, 779 cm−1

1H-NMR (CCl4)δ: 0.02 (S, 3H), 0.07 (S, 3H), 0.88 (S, 9H), 1.18-1.84(m, 4H), 2.11-2.38 (m, 2H), 3.58(S, 3H), 4.36-4.69 (m, 1H), 5.93-6.18 (m, 2H).

13C-NMR (CDCl3)δ: 173.4, 138.5, 106.1, 70.6, 51.1, 36.4, 33.9, 25.8, 20.5, 18.0, −4.5, −4.9.

EXAMPLE 3

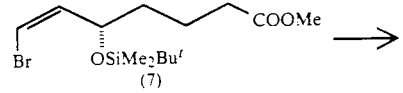

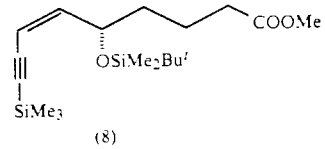

Under an argon atmosphere, CuI (58 mg, 0.31 mmol), Pd(PPh3)4 (152 mg, 0.13 mmol) were added to a solution of the compound (7) (1.54 g, 4.39 mmol), Me3-SiC≡CH (1.24 ml, 8.78 mmol), and n-PrNH2 (1.08 ml, 13.2 mmol) in benzene (20 ml). After stirring for 20 hours under room temperature in the dark place, it was poured into an aqueous saturated solution of NH4Cl. It was extracted three times with hexane, dried over MgSO₄ and concentrated to obtain the compound (8). The compound was used for the next reaction with no purification. When purified on silica gel column chromatography, the following data were obtained.

Physical Property of the Compound (8)

¹H-NMR (CCl₄)δ: 0.01 (S, 3H), 0.06 (S, 3H), 0.18 (S, 9H), 0.88(S, 3H), 1.340-1.82 (m, 4H), 2.11-2.38 (m, 2H), 1.30-1.82 (m, 4H), 2. 3.58 (S, 3H), 4.48-4.76 (m, 1H), 5.39 (d, J=11.1Hz, 1H), 5.80 (dd, J=8.4, 11.1Hz, 1H).

EXAMPLE 4

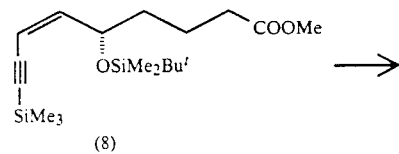
(8)

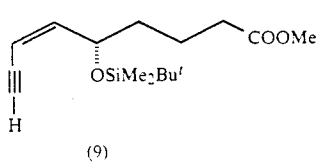
(9)

The compound (8) was dissolved in THF (15 ml), EtOH (15 ml) and H₂O (15 ml) and cooled to 0° C. AgNO₃ (2.98 g, 17.6 mmol) was added thereto. After about 15 min, KCN (2.0 g, 30.7 mmol) was dropped little by little. After stirring at 0° C. for about 3 hours, it was poured into an aqueous saturated solution of NaCl. The product was extracted for three times with hexane. The hexane layers were joined and dried over MgSO₄. The solvent was distilled off and the obtained liquid residue was purified on silica gel column chromatography, to obtain 1.24 g of the compound (9) (95.4 % yield from the compound (7)).

Physical Property of the Compound (9)

[α]²⁵_D +49.6° (c=1.15, CHCl₃).
IR (neat): 3290, 1737, 1249, 1083, 838, 774 cm⁻¹.
¹H-NMR (CCl₄)δ: 0.01 (S, 3H), 0.04 (S, 3H), 0.88 (S, 9H), 1.37-1.83 (m, 4H), 2.08-2.34 (m, 2H), 2.99 (d, J = 3.0Hz, 1H), 3.57 (S, 3H), 4.47-4.73 (m, 1H), 5.38 (dd, J=3.0, 11.1Hz, 1H), 5.87 (dd, J=8.4, 11.1Hz 1H).
¹³C-NMR (CDCl₃)δ: 173.0, 148.0, 107.4, 82.5, 79.5, 70.2, 50.8, 36.8, 33.6, 25.7, 20.4, 17.9, −4.6, −5.1.

EXAMPLE 5

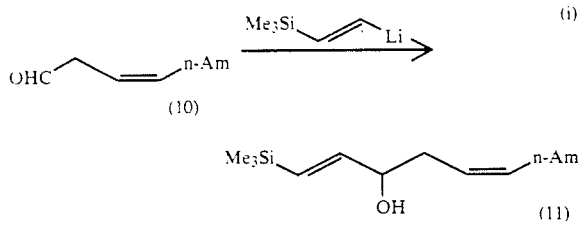

Under an argon atmosphere, a solution of 6.2 g (16 mmol) of (E)-1-tri-n-butyl tin-2-trimethylsilylethylene in THF (25 ml) was cooled to −78° C., to which n-BuLi (10 ml, 15.3 mmol) in n-hexane was dropped and stirred for one hour. The compound (10) (1.2 g, 8.2 mmol) was added to the solution and, after stirring for one hour, the organic layer incorporated with an aqueous saturated solution of NH₄Cl (10 ml) was extracted with n-hexane (50 ml×2). The collected mixed solutions were dried over MgSO₄ and concentrated under a reduced pressure. The crude product was purified on silica gel column chromatography (n-hexane/Et₂O=20/1−3/1), to obtain 1.69 g (7.0 mmol, 86%) of the compound (11).

Physical Property of the Compound (11)

¹H-NMR (CCl₄, PhH)δ: 0.10 (S, 9H), 0.90 (t, J=6.6Hz, 3H), 1.1-1.6 (m, 6H), 1.86-2.14 (m, 2H), 2.22 (t, 2H, J=6Hz), 3.98 (dt, J=4Hz, 6Hz, 1H), 5.14-5.60 (m, 2H), 5.74 (d, J=18.6Hz, 1H), 6.02 (dd, J=18.6Hz, 3.8Hz, 1H).
IR (neat): 3340, 1610, 1240, 830 cm⁻¹.
¹³C-NMR (CDCl₃)δ: 148.0, 133.3, 129.2, 124.5, 73.8, 35.1, 31.5, 29.3, 27.4, 22.4, 14.0, −1.4.

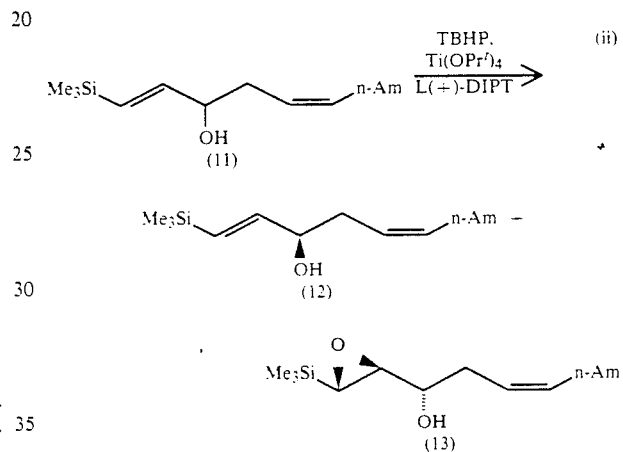

Under an argon atmosphere, a solution of Ti(OPrⁱ)₄ (0.65 ml, 2.18 mmol) in CH₂Cl₂ (15 ml) was cooled to −21° C., to which diisopropyl, L-(+)-diisopropyl tartarate (0.55 ml, 2.61 mmol) was added. After stirring for further 10 min, a solution of the compound (11) (522 mg, 3.3 ml) CH₂Cl₂ (4 ml) was added. After stirring for 10 min, 0.95 ml (3.26 mmol) of TBHP (3.397 M/CH₂Cl₂) was added and stirred at −21° C. for 3.5 hours. Me₂S (0.5 ml) was added to the reaction mixture and, after stirring at −21° C. for 30 min, the reaction solution incorporated with 0.5 ml of 10% tartaric acid was filtered with celite and concentrated under a reduced pressure. The thus obtained crude product was purified on silica gel chromatography, to obtain the compound (12) (230 mg, 44 %) and the compound (13) (243 mg, 44 %).

Physical Property of the Compound (12)

[α]²⁵_C +7.59° (c=1.37, CHCl₃).
¹H-NMR, IR and ¹³C-NMR were the same as those for the compound (11).

Physical Property of the Compound (13)

¹H-NMR (CCl₄, PhH)δ: 0.05 (S, 9H), 0.90 (t, J=6Hz, 3H), 1.1-1.7 (m, 6H), 1.87-2.18 (m, 2H), 2.15-2.38 (m, 3H), 2.62 (brs 1H), 2.73 (t, J=3Hz, 1H), 2.65 (dt, J=4Hz, 6Hz, 1H), 5.20-5.70 (m, 2H).
IR (neat): 3420, 1243, 840 cm⁻¹.
[α]²⁵_D +4.23° (c=1.13, CHCl₃).

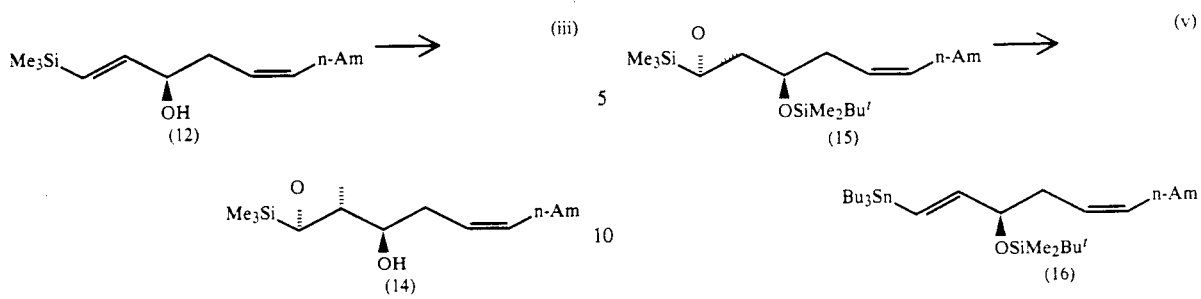

Under an argon atmosphere, 3A molecular sieve (1 g), CH$_2$Cl$_2$ (15 ml) and Ti(OPri)$_4$ (1.4 ml, 4.7 mmol) were cooled to $-20°$ C. After adding D(−)-diisopropyl tartarate (1.2 ml, 5.7 mmol) and stirring for 10 min, a solution of the compound (12) (3.65 g, 15 mmol) in CH$_2$Cl$_2$ (8 ml) was added. After cooling the liquid mixture to $-40°$ C., TBHP (4.09 M/CH$_2$Cl$_2$) (7.5 ml, 30.6 mmol) was dropped. After stirring the liquid mixture at $-21°$ C. for 4 hours, Me$_2$S (4 ml) and 10 % aqueous solution of tartaric acid (4 ml) were added and filtered through celite. The solvent was distilled off under a reduced pressure and the crude products was purified on silica gel chromatography (n-hexane/Et$_2$O=10-/1-3/1, 0.5 % Et N), to obtain the compound (14) (3.3 g, 85 %).

Physical property of the Compound (14)

$[\alpha]^{25}_D -4.25°$ (c=1.15, CHCl$_3$)

$^1$H-NMR and IR were the same as the compound (13).

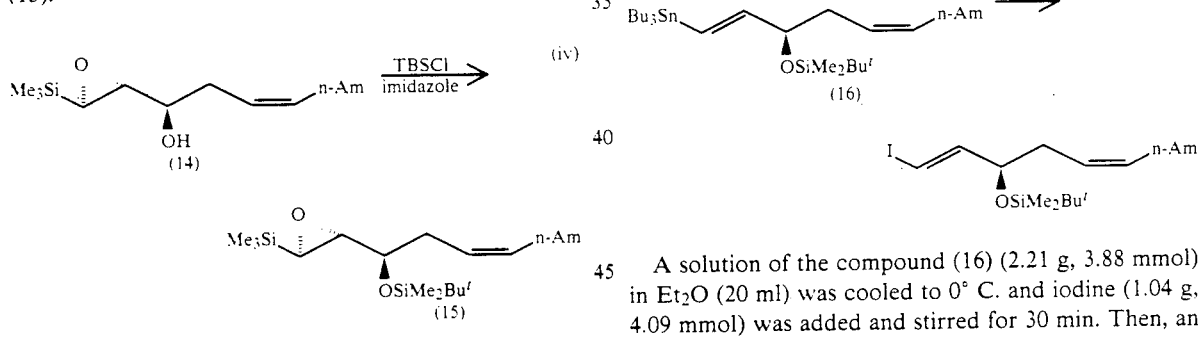

The compound (14) (2.78 g, 10.8 mmol),k imidazole 91.5 g, 22 mmol), DMF (20 ml) were cooled to 0° C. and t-butyl dimethyl chlorosilane (2.5 g, 16.5 ml) was added. After stirring the liquid mixture at room temperature for 3 hours, an aqueous solution solution of NaHCO (30 ml) was added. After extracting with n-hexane (50 ml×2), the product was dried over MgSO$_4$. After concentration, the resultant crude product was purified on silica gel column chromatography (n-hexane/Et20=50/1 −10/1, 0.5 % Et N), to obtain the compound (15) (4.04 g, −100 %).

Physical Property of the Compound (15)

$[\alpha]^{25}_D +0.18°$ (C=1.11, CHCl$_3$).

$^1$H-NMR (CCl$_4$, PhH) δ: 0.03 (S, 6H), 0.06 (S, 9H), 0.88 (m, 12H), 1.1-1.7 (m, 6H), 1.90 2.16 (m, 2H), 2.02 (d, J=3Hz, 1H), 2.26 (t, J=5 Hz, 2H), 2.59 (dd, J=4Hz, 5Hz, 1H), 3.46 (q, J=5Hz, 1H), 5.18-5.70 (m, 2H).

IR (neat): 1250, 1090, 840 cm$^{-1}$.

Bu$_3$SnH (3.5 ml, 13.0 mmol) was added at 0° C. to a THF solution (20 ml) of lithium diisopropyl amide prepared from iPr$_2$—NH (4.2 ml, 30 mmol) and nBuLi (11.0 ml, 20 mmol) and stirred for 30 min. The compound (15) (4.04 g, 10.8 mmol) was added to the liquid mixture and the organic layer was extracted with n-hexane (40 ml). The solvent was distilled off under a reduced pressure and the resultant crude product was purified on silica gel chromatography to obtain the compound (16) (5.68 g, 92 %).

Physical Property of the Compound (16)

$^1$H-NMR (CCl$_4$, PhH)δ:0.07 (S, 9H) 0.92 (m, 24H), 1.10-2.3 (m), 3.89-4.13 (m, 1H), 5.27-5.47 (m, 2H), 5.95 (m, 2H).

IR (neat): 1605, 1070, 840 cm$^{-1}$.

EXAMPLE 6

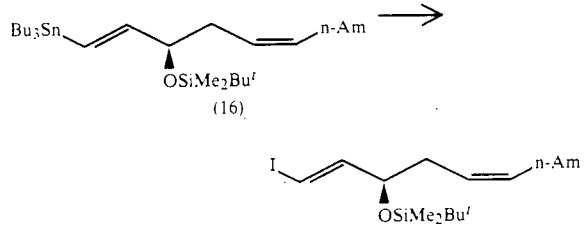

A solution of the compound (16) (2.21 g, 3.88 mmol) in Et$_2$O (20 ml) was cooled to 0° C. and iodine (1.04 g, 4.09 mmol) was added and stirred for 30 min. Then, an aqueous saturated solution of Na$_2$S$_2$O$_3$ (20 ml) was added to the liquid mixture, the product was extracted with n-hexane (30 ml), washed with an aqueous solution of 3N-NaOH and dried over MgSO$_4$.

The solvent was distilled off under a reduced pressure and the resultant crude product was purified on column chromatography (n-hexane-n-hexane/Et$_2$O=10/1), to obtain the compound (17) (1.52 g, 96%).

Physical Property of the Compound (17)

$[\alpha]^{25}_D +7.15°$ (c=2.06, CHCl$_3$).

$^1$H-NMR (CCl$_4$, PhH)δ: 0.06 (S, 9H), 0.88 (m, 12H), 1.10-1.7 (m, 6H), 1.88-2.12 (m, 2H), 2.22 (t, J=6 Hz, 2H), 4.07 (q, J=6Hz, 1H), 5.12-5.63 (m, 2H), 6.16 (d, J=15Hz, 1H), 6.47 (dd, J=6Hz, 15Hz, 1H).

IR (neat) : 1605, 1250, 1080 cm$^{-1}$.

$^{13}$C-NMR (CDCl$_3$)δ: 148.8, 132.6, 124.2, 75.6, 75.1, 35.8, 31.6, 29.3, 27.5, 25.8, 22.6, 18.2, 14.0, −4.6, −4.8.

EXAMPLE 7

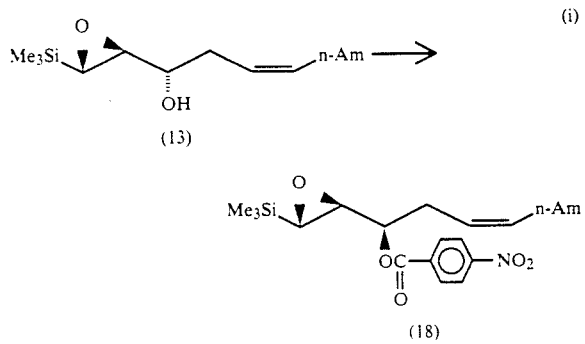

After cooling diethylazodicarboxylic acid (0.20 ml, 1.27 mmol),

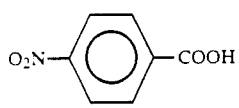

(0.22 g, 1.31 mmol) and THF (3 ml) to 0° C., a solution of pH$_3$P (350 the compound (13) (230 mg, 0.90 mmol) in THF (2 ml) was added and stirred for 30 min. An aqueous saturated solution of NaHCO$_3$ (5 ml) was added to the liquid mixture, the product was extracted with n-hexane (10 ml×2) and MgSO$_4$. The solvent was distilled off under a reduced pressure and the crude product was purified on silica gel column chromatography to obtain the compound (18) (340 mg, 93 %).

Physical Property of the Compound (18)

$^1$H-NMR (CCl$_4$, PhH)δ: 0.06 (S, 9H), 0.86 (t, J=5Hz, 3U), 1.10–1.70 (m, 6H), 1.89–2.22 (m, 3H), 2.35–2.67 (m, 2H), 2.97 (dd, J=3Hz, 7Hz, 1H), 4.78 (q, J=7Hz, 1H), 5.16–5.66 (m, 2H), 8.17 (brs, 4H).

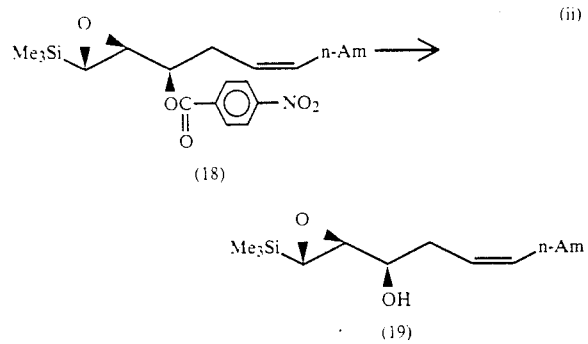

After cooling the compound (18) (40 mg, 0.8 mmol), THF (2 ml), and MeOH (2 ml) to 0° C., 2N-NaOH (2 ml) was added and stirred for one hour. An aqueous solution of NH$_4$Cl (5 ml) was added to the liquid mixture, the product was extracted with n-hexane (10 ml×3) and dried over sodium thiosulfate. The solvent was distilled off under a reduced pressure and the resultant crude product was purified on silica gel chromatography to obtain the compound (19) (214 mg, 100 %).

Physical Property of the compound (19)

[α]$^{25}$$_D$−7.40° (c=1.27, CHCl$_3$).

$^1$H-NMR (CCl$_4$, PhH)δ: 0.05 (S, 9H), 0.88 (t, J=6Hz, 3H), 1.10–1.60 (m, 6H), 1.90–2.19 (m, 2H), 2.09 (d, J=4Hz, 1H), 2.18–2.42 (m, 2H), 2.75 (t, J=5Hz, 2H), 3.10–3.45 (m, 2H), 5.18–5.62 (m, 2H).

IR (neat) 3420, 1240, 840 cm$^{-1}$.

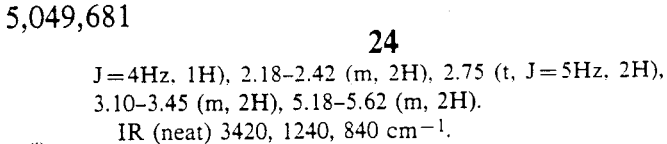

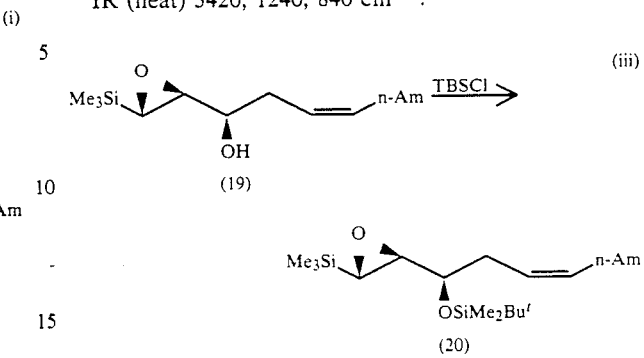

After cooling the compound (19) (214 mg, 0.83 mmol), DMF (2 ml and imidazole (120 mg, 1.76 mmol) to 0° C., TBSCl (190 mg, 1.26 mmol) was added and stirred at room temperature for 3 hours. An aqueous saturated solution of NaHCO$_3$ (5 ml) was added to the liquid mixture, extracted with n-hexane (20 ml) and dried over MgSO$_4$. The resultant crude product was purified on silica gel column chromatography to obtain the compound (20) (285 mg, 92 %).

Physical value for the Compound (20)

$^1$H-NMR (CC14, PhH)δ: 0.06 (S, 15H), 0.91 (m, 12H), 1.15–1.7 (m, 6H), 1.86–2.33 (m, 5H), 2.62 (dd, J=3Hz, 7Hz, 1H), 3.14 (q, J=7Hz, 1H), 5.13–5.58 (m, 2H).

IR (neat) 1250, 1090, 840 cm$^{-1}$.

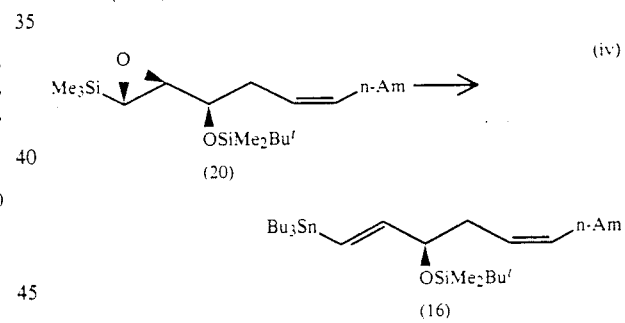

Bu$_3$SnH (1.3 ml, 4.83 mmol was added at 0° C. to a THF solution (10 ml) of lithium diisopropyl amide prepared from iPr$_2$NH (1.75 ml, 12.5 mmol) and nBuLi (5.3 ml, 8.2 mmol) and stirred for one hour. The compound (20) (1.54 g, 4.1 mmol) was added and stirred at room temperature for 2 hours. An aqueous solution of NaCl (10 ml) was added to the liquid mixture, the organic layer was extracted with n-hexane and dried over MgSO$_4$. The solvent was distilled off under a reduced pressure and the resultant crude product was purified on silica gel chromatography, to obtain the compound (16) (2.22 g, 95%).

EXAMPLE 8

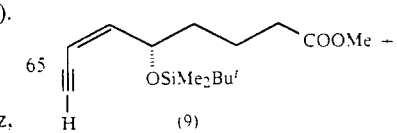

25
-continued

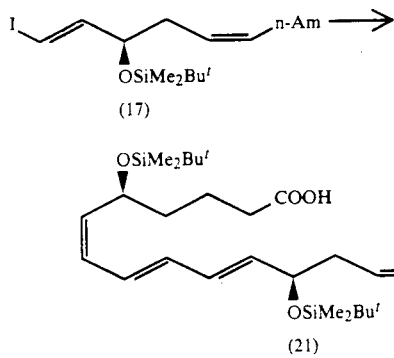

(17)

(21)

THF solution of disiamylborane (8.7 ml, 0.5 M, 4.38 mmol) prepared from THF solution of BH (1 M) and THF solution of 2-methyl-2-butene (2 M) was dropped to a solution of the compound (9) (863 mg, 0.92 mmol) in THF (25 ml) cooled to 0° C. After stirring at 0° C. for one hour and confirming that the compound (9) was eliminated by TLC (thin layer chromatography), an aqueous solution of 2N-NaOH (8.75 ml, 17.5 mmol) was added slowly. After 10 min, the compound (17) (1.67 g, 4.09 mmol) and Pd(PPh$_3$)$_4$ (1.67 mg, 0.15 mmol were added. After vigorously stirring the mixture for 16 hours while heating at about 50° C., it was poured into an aqueous saturated solution of NH$_4$Cl, and the product was extracted with ether for three times. The ether layers were collected and dried over MgSO$_4$. The ether was distilled off and the liquid residue was purified on silica gel column removed with oxygen, to obtain 1.16 g (70.4% yield) of the compound (21).

Physical Property of the compound (21)

IR (neat) 3000, 1706, 1252, 1080, 836, 774 cm$^{-1}$.

$^1$H-NMR (90 MHz, CDCl$_3$)δ: 0.02 (S, 3H), 0.04 (S, 9H), 0.85 (S, 12H), 0.88 (S, 9H), 1.1-2.5 (m, 16H), 3.16 (q, J=6.5Hz, 1H), 4.36-4.67 (m, 1H), 5.2-6.7 (m, 8H).

$^1$H-NMR (500MHz, CDCl$_3$)δ: 0.02 (S, 3H), 0.05 (S, 6H), 0.07 (S, 3H), 0.88 (t, 3H), 0.88 (S, 9H), 0.91 (S, 9H), 1.23-1.78 (m, 10H), 2.01 (q, J=7Hz, 2H), 2.22-2.38(m, 4H), 4.18 (q, J=7Hz, 1H), 4.57 (q, J=7Hz, 1H), 5.38 (m, 2H), 5.44 (dt, J=12, 7Hz, 1H), 5.72 (dd, J= 7,14Hz, 1H), 5.96 (t, J=12Hz, 1H;, 6.19 (m, 2H), 6.36 (dd, J=12, 14Hz, 1H)

$^{13}$C-NMR (22.5MHz, CDCl$_3$ )δ: 179.8, 137.8, 134.9, 133.8, 132.0, 129.3, 128.1, 127.1, 125.2, 73.3, 68.8, 37.8, 36.5, 34.1, 31.6, 29.4, 27.5, 26.0, 22.6, 20.7, 18.3, 18.2, 14.1, −4.1, −4.3, −4.7.

[α]$^{25}$$_C$+4.33° (c=0.60, CHCl$_3$ ).

EXAMPLE 9

(21)

26
-continued

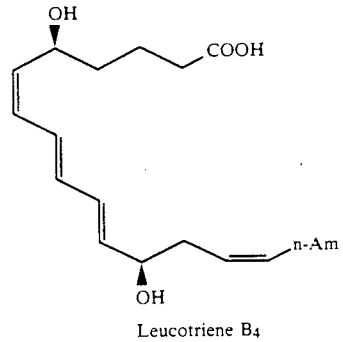

Leucotriene B$_4$

Under an argon atmosphere, n-Bu$_4$NF (11.5 ml, 11.5 mmol, 1 mol in THF) was added into a solution of the compound (21) (648 mg, 1.15 mmol) in THF 15 ml) and stirred at room temperature for 18 hours. The reaction was poured into McIlvaine's buffer solution (pH— 4) and extracted with ether. The organic layer was washed with the buffer solution once again and finally washed with unsaturated aqueous solution of sodium chloride. A fresh ether was prepared and used for the back extraction of the buffer solution and the saturated aqueous solution of sodium chloride used above. The procedures were repeated for three times and the ether solution was dried over anhydrous magnesium sulfate. The ether was distilled off under a reduced pressure and the residue was purified on silica gel column chromatography, to obtain 310 mg (80.2% yield) of leucotriene B$_4$.

Physical Property of the Leucotriene B$_4$

[α]$^{25}$$_D$+13.1° (c=0.26, CDCl$_3$).

lit [α]$^{25}$$_D$+12.6° (c=0.46, CDCl$_3$): JOC, 51, 1253 (1986).

EXAMPLE 10

Me$_3$Si ⌇ CHO  Br⌇  →
                    Zn
(21)

Me$_3$Si ⌇⌇⌇ ≡H
            OH
            (22)

To a mixture of the aldehyde (21) (20 g, 156 ml) and Zn dust (15.3 g, 234 mmol) in THF (200 ml) was added TiCl$_4$ (0.1 ml) at 0° C. The mixture was stirred at 0° C. for 5 min. Propagyl alcohol (21 ml, 234 mmol) dissolved in THF (20 ml) was added dropwise over 20 min. The mixture was stirred at room temperature for 30 min, and H$_2$O (8.4 ml, 468 mmol) and hexane (200 ml) were added. The mixture was vigorously stirred for 1 hour and then filtrated through a pad of silica gel. Evaporation of the filtrate gave an oil which was semi-purified by passing through a short silica gel column using a mixture of hexane and Et$_2$O (5: 1) as an eluent to give the adduct (22) (29 g, 100%).

R$_f$ 0.32 (hexane: Et$_2$O=3:1)

IR (neat) 3370, 3290, 1620, 1245, 840 cm$^{-1}$ $^1$H NMR (CCl$_4$, RhH)δ 0.10 (s, 9H), 1.91 (t, J=3Hz, 1H), 2.31 (dd, J=6, 3Hz, 1H), 2.90 (br s, 1H), 4.11 (dt, J=3.3, 6Hz, 1H), 5.80 (d, J=18Hz, 1H), 6.10 (dd, J=3.3, 18Hz, 1H).

EXAMPLE 11

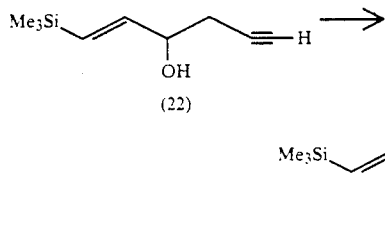

To an ice-cooled solution of the alcohol (22) (11.4 g, 83 mmol) and p-TsOH H₂O (160 mg) in Ch₂Cl (280 ml) was added ethyl vinyl ether (15.9 ml, 166 mmol) dropwise. After completion of the addition, the solution was stirred at 0° C. for 30 min, and poured into a mixture of saturated NaHCO₃ aq. solution and hexane. The product was extracted with hexane twice. The combined organic layers were dried with MgSO₄ and concentrated to leave an oil, which was chromatographed on silica gel using a mixture of hexane and Et₂O containing 1% of Et₃N to give the ether (23) (14.8 g, 75% yield).

$R_f$ 0.53 (hexane: Et₂O=5 1).

IR (neat) 3280, 1618, 1139, 1085, 840 cm⁻¹.

¹H NMR (CCl₄, CH₂Cl₂)δ0.10 (s, 9H), 0.99–1.32 (m, 6H), 1.77–1.88 (m, 1H), 2.19– 2.40 (m, 2H), 3.10–3.62 (m, 2H) 3.88–4.16 m, 1H), 4.44 4.79 (m, 1H), 5.59–6.12 (m, 2H).

EXAMPLE 12

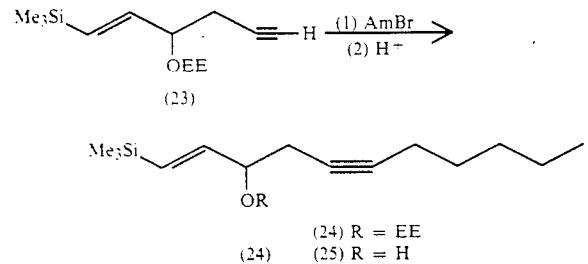

To a well stirred stirred solution if (23) and bipyridyl (ca 10 mg) in THF was added n-BuLi (6.7 ml, 10.5 mmol), 1.56 M in hexane) dropwise at −60° C. The solution was stirred at −60° C. for 1 hour. To the solution, HMPA (5.2 ml, 30 mmol) and n-C₅H₁₁Br (1.86 ml, 15 mmol) were added and stirring was continued for 1.5 days at room temperature. The solution was poured into water and the product was extracted with hexane repeatedly. The combined organic layers were dried with MgSO₄ and concentrated to leave the crude product (24).

A solution of the crude product (24) in MeOH (70 ml) and 3 N HCl (10 ml) was stirred at room temperature for 20 min and poured into brine. The product was extracted with hexane three times. The combined extracts were dried with MgSO₄ and concentrated to leave an oil, which was chromatographed on silica gel to give the alcohol (25) (1.84 g, 77.3%).

$R_f$ 0.47 (hexane: Et₂O=3:1).

IR (neat) 3370, 3290, 1621, 1245, 837 cm⁻¹.

¹H NMR (CCl₄, PhH)δ0.12 (s, 9H), 0.94 (t, J=6Hz, 3H), 1.1–1.7 (m, 6H), 1.99–2.45 (m, 4H), 2.92 (br s, 1H), 3.94–4.22 (m, 1H), 5.87 (d, J=18Hz, 1H), 6.03 (dd, J=3, 18Hz, 1H),

¹³C NMR (CDCl₃)δ146.4, 130.2, 83.2, 75.5, 72.4, 31.0, 28.6, 27.6, 22.1, 18.6, 13.8, −1.5.

EXAMPLE 13

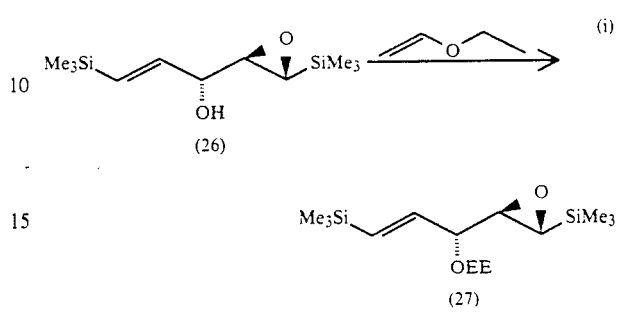

A solution of (26) (4.3 g, 17.6 mmol), ethyl vinyl ether (5.1 ml, 52.8 mmol), and PPTS (885 mg, 3.52 mmol) in CH₂Cl₂ (30 ml) was stirred at room temperature for 3 hours and poured into saturated NaHCO₃ solution. The product was extracted with hexane twice. The combined organic layers were dried (MgSO₄) and evaporated to leave an oil, which was purified by chromatographed on silica gel by using hexane-Et₂O containing 1% of Et₃N as an eluent to give the ether (27) (5.54 g, 100% yield).

$R_f$ 0.71 (hexane: Et₂O=4:1).

¹H NMR (CCl₄, PhH)δ 0.03 and 0.07 (2S, 18H), 0.99–1.32 (m, 6H), 1.98–2.15 (m, 1H), 2.53–2.73 (m, 1H), 3.20–3.66 (m, 2H), 3.72–3.94 (m, 1H), 4.49–4.82 (m, 1H), 5.68–6.03 (m, 2H).

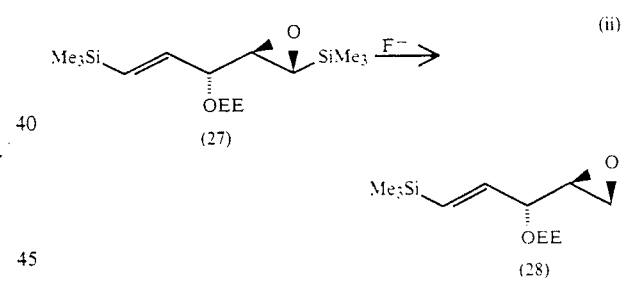

To a solution of (27) (3.08 g, 9.74 mmol) in DMSO (20 ml) was added a solution of n-Bu₄NF (16.0 ml, 11.7 mmol, 0.73 M in THF) at room temperature. The resulting solution was stirred at room temperature overnight and poured into brine. The product was extracted with hexane twice. The organic layers were dried (MgSO₄) and concentrated to leave an oil, which was purified by chromatography on silica gel using hexane-Et₂O containing 1% of Et₃N as an eluent to afford (28) (2.08 g, 88% yield).

$R_f$ 0.44 (hexane Et₂O=4:1).

IR (neat) 1095, 844 cm⁻¹.

¹H NMR (CCl₄, PhH)δ 0.17 (s, 9H), 0.9–1.5 (m, 6H), 2.25–2.92 (m, 3H), 3.21–3.66 (m, 2H), 3.83–4.02 (m, 1H), 4.48–4.80 (m, 1H), 5.79–6.02 (m, 2H).

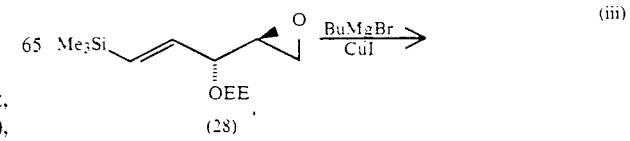

-continued

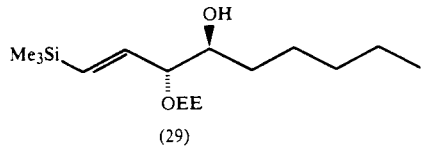

(29)

A solution of CuI (267 mg, 1.4 mmol) and Me₂S (1 ml) in Et₂O (30 ml) was cooled to −60° C. and n-BuMgBr (18.3 ml, 21 mmol, 1.15 M in Et₂O) was added dropwise. The solution was stirred at −60° C. for 20 min, after which the epoxide (28) (3.42 g, 14.0 mmol) dissolved in Et₂O (5 ml) was added. The solution was gradually warmed up to room temperature over 2 hours and poured into saturated NH₄Cl solution. The product were dried (MgSO₄) and concentrated to give the crude product. Purification by chromatography on silica gel gave the alcohol (29) (3.75 g, 89% yield).

R$_f$ 0.20 and 0.26 (hexane: Et₂O=4:1).
IR (neat) 3440, 1614, 1084, 837 cm$^{-1}$.
$^1$H NMR (CCl₄, PhH)δ0.18 (s, 9H), 0.8–1.7 (m, 17H), 2.2–2.5 (m, 1H), 3.14–4.11 (m, 4H), 4.48–4.78 (m, 1H), 5.64–6.21 (m, 2H).

EXAMPLE 14

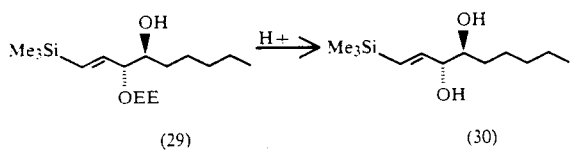

To a solution of the ether (29) (2.2 g, 7.28 mmol) in MeOH (15 mL) was added 3 drops of 3 N HCl solution at room temperature. The solution was stirred for 30 min and poured into saturated NaHCO₃ solution. The product was extracted with Et₂O 3 times. The combined organic layers were dried (MgSO₄) and concentrated. The residue was purified by chromatography on silica gel to afford the diol (30) (1.72 g, 100% yield).

R$_f$ 0.50 (hexane: AcOEt=1:1).
IR (neat) 3350, 1615, 1245, 860, 835 cm$^{-1}$.
$^{13}$C NMR (CDCl₃)δ 143.5, 132.9, 77.5, 74.2, 31.8, 25.5, 22.5, 14.0, −1.3.
$^2$H NMR (CCl₄, PhH)δ 0.07 (s, 9H), 0.83 (t, 3H, J=6Hz), 0.97–1.60 (m, 8H), 2.43 (d, 1H, J=5Hz), 2.68 (d, 1H, J=5Hz), 3.40–3.70 (m, 1H), 3.99 (q, 1H, J=4Hz), 5.67–6.16 (m, 2H).

EXAMPLE 15

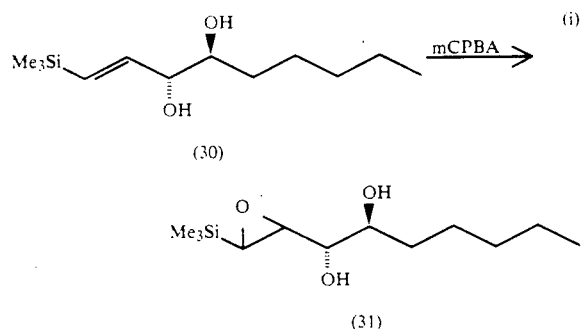

A mixture of (30) (1.34 g, 5.82 mmol), m-CPBA (1.88 g, 8.73 mmol, 80% content), and NaHCO₃ (1 47 g, 17.5 mmol) in CH₂Cl₂ (12 ml) was stirred at room temperature overnight and Me₂S (ca 1 ml) was added to quench excess m-CPBA. To the mixture, saturated NaHCO₃ solution was added. After stirring for 15 min, the product was extracted twice. The combined extracts were dried (MgSO₄) and concentrated to leave an oil, which was purified by chromatographed on silica gel to afford the epoxide (31) (1.05 g, 75% yield).

R$_f$ 0.37 (hexane AcOEt=1:1).
$^1$H NMR (CCl₄, PhH)δ0.18 (s, 9H), 0.8–1.9 (m, 11H), 2.16–2.38 (m, 1H), 2.8–4.3 (m, 5H).

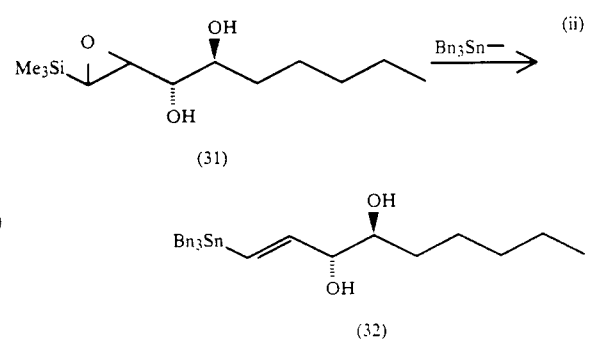

An ice-cooled solution of LDA in THF was prepared in a usual way from HNPr₂ (1.0 ml, 20.9 mmol), n-BuLi (9.6 ml, 14.9 mmol, 1.56 M in hexane), and THF (40 ml). To this solution were added bipyridyl (ca 10 mg) and (31) (734 mg, 2.98 mmol) dissolved in THF (5 ml) at 0° C. After 15 min. n-Bu₃SnH was added to the solution and stirring was continued for 20 hours at room temperature. The solution was poured into brine and the product was extracted with Et₂O 3 times. The combined extracts were dried (MgSO₄) and concentrated to leave an oil, which was chromatographed on silica gel to give the product (32) (692 mg, 54% yield).

R$_f$ 0.59 (hexane: Et₂O=1:3).
IR (neat) 3360, 1596, 1456, 1062, 997 cm$^{-1}$.
$^1$H NMR (CCl₄)δ 0.7–2.0 (m), 2.9–3.7 (m, 3H), 3.86–4.08 (m, 1H), 5.60–6.47 (m, 2H).

EXAMPLE 16

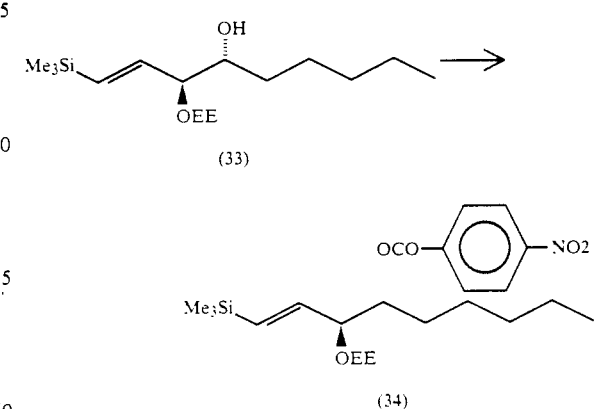

To an ice-cooled solution of the alcohol (33) (2.0 g, 6.62 mmol), p-nitrobenzoic acid (1.86 g, 9.93 mmol), and PPh₃ (2.78 g, 10.6 mmol) in THF (22 ml) was added DEAD (1.46 ml, 9.27 mmol) dropwise. The solution was stirred at 0° C. for 2 hours, after which saturated NaHCO₃ solution was added. The mixture was stirred for 1 hour at room temperature and poured into brine.

The product was extracted with hexane 3 times. The combined organic phases were dried (MgSO₄) and concentrated to give an oil, which was purified by chromatography on silica gel using hexane-Et₂O containing 1% of Et₃N as an eluent to give the benzoate (34) (2.07 g, 69% yield).

R_f 0.47 (hexane: Et₂O=4:1).

IR (neat) 1724, 1530, 1271, 1103, 839 cm⁻¹.

¹H NMR (CCl₄, PhH)δ 0.10 (s, 9H), 0.8–2.0 (m, 17H), 3 24–3.70 (m, 2H), 4.02 4.30 (m, 1H), 4.46–4.78 (m, 1H), 4.98–5.29 (m, 1H) 5.86–6.01 (m, 1H), 8.02–8.31 (m, 4H).

EXAMPLE 17

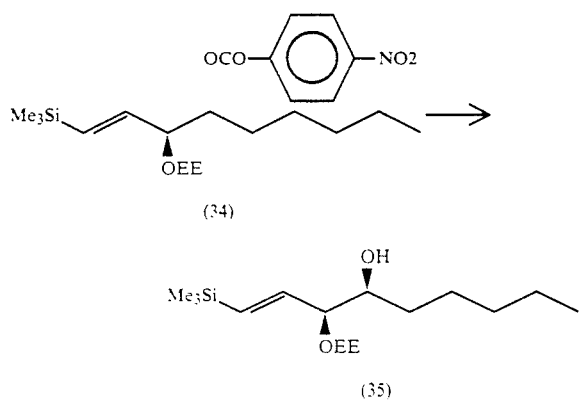

To an ice-cooled solution of the benzoate (34) (2.07 g, 4.59 mmol) in MeOH (10 ml) and THF (10 ml) was added 3 N NaOH solution 10 ml). The solution was stirred at 0° C. for 3 hours then at room temperature for 1 hour and poured into brine. The product was extracted with hexane 3 times. The combined extracts were dried (MgSO₄) and concentrated to leave an oil, which was purified by chromatography on silica gel with hexane-Et₂O containing 1% Et₃N to afford the alcohol (35) (1.33 g, 96% yield).

R_f 0 25 and 0.32 (hexane: Et₂O=4:1).

¹H NMR (CCl₄, PhH)δ 0.08 (s, 9H), 0.8–1.7 (m, 17H) 2.49–2.78 (m, 1H), 3.13–3.88 (m, 4H), 4.49–4.74 (m, 1H), 5.62–6.14 (m, 2H).

EXAMPLE 18

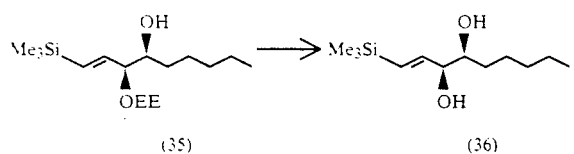

A solution of (35) (1.33 g, 4.40 mmol) and PPTS (221 mg, 0.88 mmol) in MeOH (10 ml) was stirred at room temperature for 5 hours and poured into saturated NaHCO₃ solution. The product was extracted with Et₂O 3 times and the combined extracts were dried (MgSO₄) Concentration and chromatography on silica gel afforded the diol (36) (980 mg, 97% yield).

R_f 0.50 (hexane: AcOEt=1:1).

IR (neat) 3340, 1247, 882, 839 cm⁻¹.

¹H NMR (CDCl₃)δ0.08 (s, 9H), 0.7–1.6 (m, 11H), 3.09 (d, J=4.7Hz, 1H), 3.28 (m, J=4.7Hz, 1H), 3.25–3.52 (m, 1H), 3.66 3.97 (m, 1H), 5 90–6.04 (m, 2H).

¹³C NMR (CDCl₃)δ 145.1, 132.6, 77.8, 74.3, 32.9, 31.8, 25.2, 22.5, 13.9, −1.4.

EXAMPLE 19

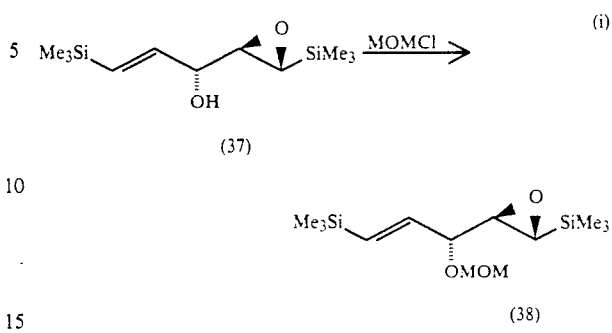

To an ice-cooled suspension of oil free NaH (prepared from NaH (1.18 g, 50% in oil) by washing with hexane) in THF (80 ml) was added the alcohol (38) (4.0 g, 16.4 mmol) dissolved in THF (7 ml). The mixture was stirred at 0° C. for 10 min and MOMCl (1.49 ml, 19.7 mmol) was added dropwise. Stirring was continued at room temperature for 7 hours, after which water was added carefully until the gas evolution coased. The mixture was poured into saturated NH₄Cl solution and extracted with hexane twice. The combined extracts were dried (MgSO₄) and concentrated to leave an oil which was chromatographed on silica gel to give the MOM other (38) (3.99 g, 85% yield).

R_f 0.56 (hexane: Et₂O=4:1).

¹H NMR (CCl₄, phH)δ 0.12 (s, 9H), 2.03–2.21 (m, 1H), 2.59–2.85 (m, 1H), 3.25 (s, 3H), 3.68–3.90 (m, 1H),4.52 (br s, 2H), 5.94 (br s, 2H).

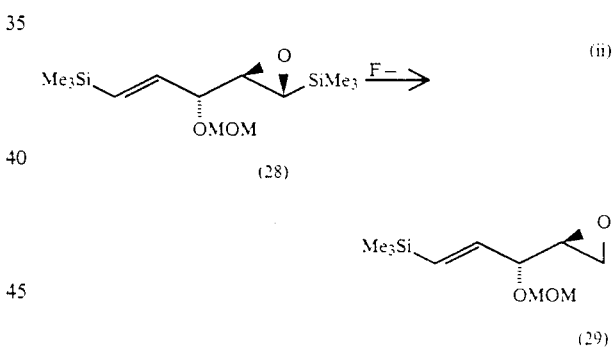

To a solution of (28) 3.99 g, 13.9 mmol) in DMSO (50 ml) was added n-Bu₄NF (28.5 ml, 20.7 mmol, 0.73 M in THF). The solution was stirred at room temperature for 7 hours and poured into brine. The product was extracted with hexane 3 times and the combined extracts were dried (MgSO₄) and concentrated to give an oil, which was purified by chromatography on a silica gel to give (29) (2.71 g, 91% yield).

R_f 0.32 (hexane: Et₂O=4:1).

¹H NMR (CCl₄, PhH)δ 0.11 (s, 9H), 2.16–2.96 (m, 3H), 3.22 (s, 3H), 3.79–3.98 (m, 1H), 4.49 (s, 2H), 5.92 (s, 2H).

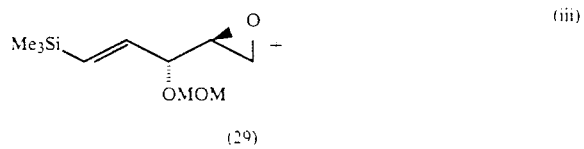

-continued

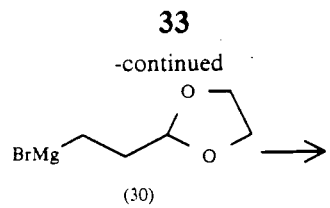

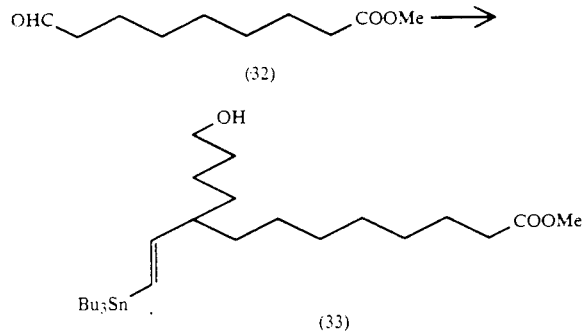

To product (31) (1.07 g, 61 % yield) was obtained from (29) (1.2 g, 5.55 mmol), CuI (317 mg, 1.67 mmol), Me$_2$S (1 ml), and the Grignard reagent (30) (17.1 ml, 11.1 mmol), 0.65 M in THF) in Et$_2$O (25 ml) by the procedure shown in Example 13-(iii) (vide supra).

R$_f$ 0.15 (hexane: Et$_2$O = 1:1).

$^1$H NMR (CCl$_4$, PhH)δ 0.13 (s, 9H), 1.0–1.8 (m, 12H), 2.7 (br s, 1H), 3.15–4.17 (m, 8H), 4.48–4.84 (m, 2H), 5.66–6.21 (m, 2H).

EXAMPLE 20

A solution of (E)-Bu$_3$SnCH=CHSnBu$_3$ (12.3 ml, 23.3 mmol) in THF (5 ml) was cooled to −70° C., to which solution a of n-BuLi (13.7 ml, 21.3 mmol; 1.56 M) in hexane was dropped. After stirring at 70° C. for one hour, (E)-Bu$_3$SnCH=CHLi could be prepared. The anions were dropped into a solution of the aldehyde (32) (3.61 g, 19.4 mmol) in THF (60 mll) at −70° C. After the completion of the dropping, they were stirred at −70° C. for one hour. The reaction solution was poured into a mixed solution of hexane and aqueous saturated solution of ammonium chloride and the product was extracted twice with hexane. The hexane layer was dried over MgSO$_4$ and concentrated. When the residue was purified on silica gel column chromatography, 3.93 g (40.3%) of the alcohol (33) was obtained.

R$_f$ 0.52 (hexane: Et$_2$O = 1:1).

$^1$H NMR (CCl$_4$) δ 0.7–1.9 (m), 2.07–2.60 (m, 3H), 3.54 (s, 3H), 3.78–4.03 (m, 1H), 5.2–6.4 (m, 2H).

EXAMPLE 21

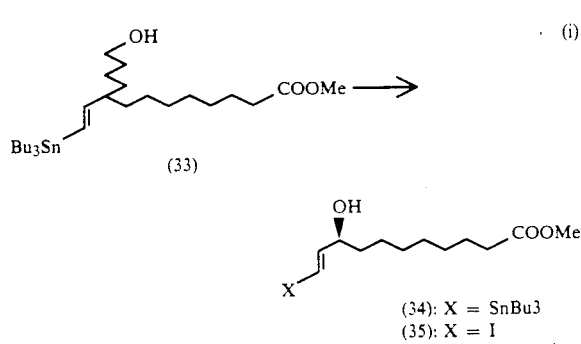

The compound (33) (2.53 g, 5.03 mmol), 3A molecular sieve (550 mg), Ti(O-iPr)$_4$ (0.45 ml, 1.5 mmol), D-(−)-DIPT (0.38 ml, 1.81 mmol), tBuOOH (2.24 ml, 7.55 mmol; 3.37 M) in CH$_2$Cl$_2$ and CH$_2$Cl$_2$ (21 ml) were reacted at −21° C. for 1.5 days. Usual after treatment was applied by adding Me$_2$S (4 ml) and using an aqueous 10% solution of tartaric acid (2 ml), Et$_2$O (60 ml), celite (4 g) and NaF (5 g), to obtain the compound (34) as a crude product.

The crude product (34) was dissolved in Et$_2$O (30 ml) and cooled to 0° C. Then, I$_2$ was added to the solution till the color of I$_2$ disappeared (about 1.3 g). After 30 min, an aqueous solution of sodium thiosulfate was added and the product was extracted twice with hexane. The hexane layer was dried over MgSO$_4$ and when purified on silica gel chromatography 703 mg (41.1%) of the compound 3 was obtained. The optical purity of the compound (35) was higher than 99% (MTPA analysis).

[α]$^{25}_D$ + 3.75° (c = 2.24, CHCl$_3$).

$^1$H NMR (CCl$_4$)δ 1.1–1.7 (m, 12H), 2.18 (t, J=7Hz, 1H), 2.88 (br s, 1H), 3.55 (s, 3H), 3.78–4.06 (m, 1H), 6.18 (d, J=1.5Hz, 1H), 6.43 (dd, J=5.4, 15Hz, 1H).

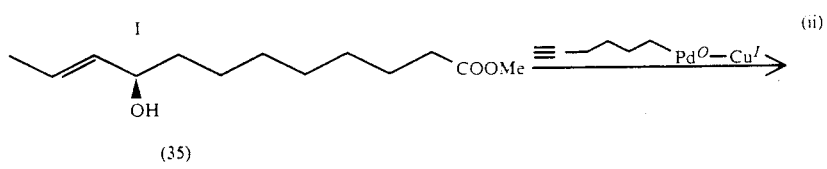

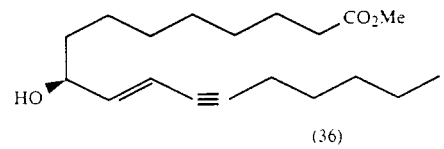

Under an argon atmosphere, Pd(PPh)$_4$ (50 mg, 0.043 mmol) and CuI (40 mg, 0.21 mmol) were added to a solution of the compound (35) (302 mg, 0.98 mmol), 1-heptyne (0.25 ml) and nPrNH$_2$ in benzene (3 ml). After stirring at room temperature for 3 hours, an aqueous saturated solution of NH$_4$Cl (5 ml) was added and extracted with Et$_2$O (10 ml × 2). The organic layer was dried over MgSO$_4$ and, after filtration, the solvent was distilled off under a reduced pressure. The crude product was purified on silica gel chromatography to obtain the compound (36) (260 mg, 0.84 mmol, 86.0%).

$^1$H NMR (CCl$_4$, TMS) 0.87 (t, 3H, J=6Hz), 1.10-1.83 (m, 18H), 2.05-2.35 (m, 4H), 2.91 (brs, 1H), 3.54 (s, 3H), 3.83-4.09 (m, 1H), 5.46 (d, 1H, J=16Hz), 5.87 (dd, 1H, J=6Hz, 16Hz).

IR (neat) 3410, 1725, 1440 cm$^{-1}$.

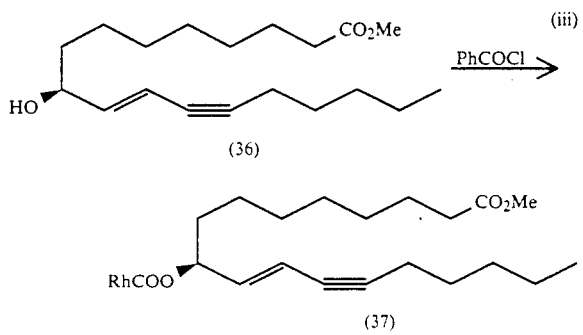

PhCOCl (0.15 ml, 1.29 mmol) was added to a solution of the compound (36) (210 mg, 0.68 mmol) in pyridine (3 ml) and stirred at room temperature for 3 hours. Hexane (5 ml) and an aqueous solution of NaHCO$_3$ (5 ml) were added to the liquid mixture and extracted with hexane-Et$_2$O (2/1, 20 ml×2). The organic layer was dried over MgSO$_4$ and, after filtration, the solvent was distilled off under a reduced pressure. The thus obtained crude product was purified on silica gel chromatography to obtain the compound (37) (290 mg, 100%).

$^1$H NMR (CCl$_4$, TMS) 0.87 (t, 3H, J=6Hz), 1.0-1.9 (m, 18H), 2.05-2.35 (m, 4H), 3.54 (S, 3H), 5.38 (q, 1H), 5.62 (dt, 1H, J=15Hz, 1Hz), 5.94 (dd, 1H, J=7Hz, 14Hz), 7.20-8.05 (m, 5H)

IR (neat) 1720, 1610, 1365, 710 cm$^{-1}$.

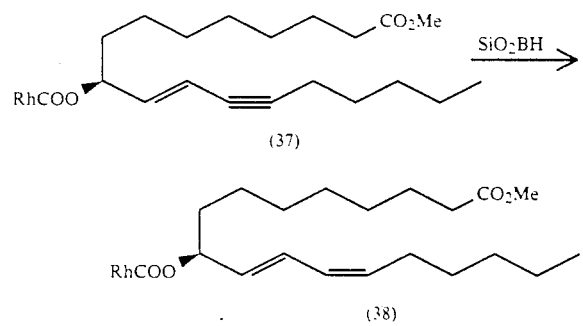

Under an argon atmosphere, a solution of the compound (37) (102 mg, 0.24 mmol) in THF (1 ml) was cooled to 0° C. and then 0.5 M SiO$_2$BH (0.8 ml, 0.4 mmol) was added. After stirring for 2 hours, AcOH (0.01 ml) was added under stirring at 40° C. for 3 hours. Water (2 ml) was added to the reaction solution and extracted with hexane-Et$_2$O (2/1, 10 ml×2). After drying the organic layer on MgSO$_4$ and filtration, the solvent was distilled off under a reduced pressure. The thus obtained oily product was dissolved in Et$_2$O (5 ml) and, after cooling to 0° C., 1 N NaOAc (1.5 ml) and 35% H$_2$O$_2$ (0.3 ml) were added and stirred for 10 min. Et$_2$O (10 ml) and a saturated aqueous solution of NH$_4$Cl (10 ml) were added to the reaction solution and extracted with Et$_2$O-hexane (1/1, 10 ml×1). The thus obtained crude product was purified on silica gel chromatography to obtain the compound (38) (70 mg, 70%).

270 MHz $^1$H NMR (CDCl$_3$, TMS)δ 0.87 (t3H, J=6.6Hz), 1.15-1.45 (m, 14H), 1.47-1.90 (m, 4H), 2.165 (q, 2H, J=20Hz), 2.29 (t, 2H, J=7.4Hz), 3.66 (s, 3H), 5.42-5.60 (m, 2H), 5.68 (dt, 1H, J=15.0Hz, 7.4Hz), 5.94 (t, 1H, J=10.9Hz) 6.60 (dd, 1H, J=11.2Hz, 15.1Hz), 7.40-7.62, 8.00-8.11 (m, 5H).

$^{13}$C NMR δ 174.1, 165.8, 133.8, 132.7, 130.8, 129.5, 128.2, 127.5, 75.3, 541.3, 34.7, 34.0, 31.4, 29.2, 29.0, 27.7, 25.1, 24.9, 22.5, 14.0.

IR (neat) 1720, 1605, 1265, 710 cm$^{-1}$.

$[α]^{22}_D$ +69.2° (c=1.0, CHCl$_3$).

When the compound (38) was hydrolyzed, dimorpherocid acid (39) known as anti bacteria substance for orizae blast was obtained.

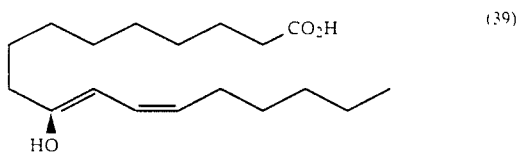

EXAMPLE 22

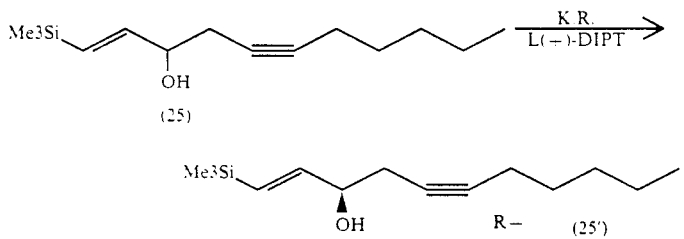

Under an argon atmosphere, a solution of Ti(OiPr)$_4$ (2.55 ml, 7.55 mol) in CH$_2$Cl$_2$ (35 ml) was cooled to 20° C., to which L-(+)-DIPT (1.90 ml, 9.04 mmol) were added and stirred for 20 min. Successively, the solution of the compound (25) (1.80 g, 7.55 mmol) in CH$_2$Cl$_2$ (5 ml) was added and stirred for 15 min. Then, after dropping a solution of TBHP (3.3 ml, 11.55 mmol; in 3.5 M) in CH$_2$Cl$_2$, and stirring at −21° C. for 4 hours, Me$_2$S (1 ml) was added and stirred for 30 min. Then, aqueous 10% solution of tartaric acid (1 ml) and NaF (2 g) were

EXAMPLE 24

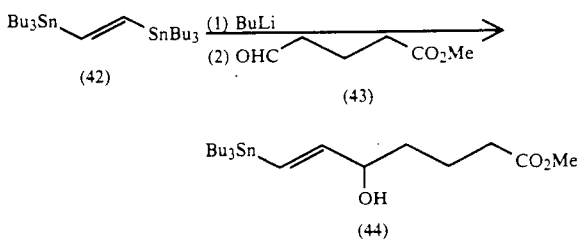

added, stirred for one hour, filtered through celite and the solvent was distilled off under a reduced pressure. The thus obtained crude product was dissolved in Et$_2$O (60 ml) and cooled to 0° C. After adding an aqueous 1N solution of NaOH (30 ml) and vigorously stirring for 30 min. the organic layer was extracted, dried over MgSO$_4$, filtered and then the solvent was distilled off under a reduced pressure. The resultant mixture of the compounds (25') and (40) was separated and purified on SiO$_2$ column chromatography to obtain the compound (25') (0.75 g, 41.7%) and the compound (40) (0.82 g, 41.1%).

IR (neat) 3370, 3290, 1621, 1245, 837 cm$^{-1}$.

$^1$H NMR (CCl$_4$, PhH)δ 0.12 (s, 9H), 0.94 (t, j=6Hz, 3H), 1.1–1.7 (m, 6H), 1.99–2.45 (m, 4H), 2.92 (br s, 1H), 3.94–4.22 (m, 1H), 5.87 (d, J=18Hz, 1H), 6.03 (dd, J=3, 18Hz, 1H).

$[α]^{35}_D$ −55.3° (c=1.25, acetone).

$^1$H NMR (CCl$_4$, PhH)δ 0.07 (S, 9H), 0.88 (t, 3H, J=6Hz) 1.10–1.70 (m, 6H), 1.90–2.15 (m, 2H) 2.28 (d, 1H, J=4Hz), 2.33 (dt, 2H, J=6Hz, 2.5Hz) 2.62 (brs, 1H, OH) 2.84 (t, 1H, J=4Hz) 3.64 (dt, 1H, J=4Hz, 6Hz).

IR (neat) 3440, 1250, 890, 835 cm$^{-1}$.

$[α]^{25}_D$ +16.1° (c=1.65, CHCl$_3$).

EXAMPLE 23

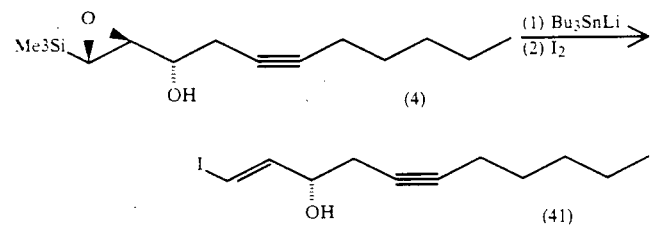

Under an argon atmosphere, a mixed solution of THF (5 ml) and iPrNH (0.70 ml, 50 mmol) was cooled to 0° C., to which n-BuLi (20 ml, 3.6 mmol, b 1.8 M) in hexane was added. After stirring for 30 min, n-Bu$_3$SnH (0.85 ml, 3.1 mmol) was added. After stirring for further 30 min, adding the compound (40) (366 mg, 1.43 mmol) and stirring at 0° C. for 30 min and further at room temperature for 3 hours, water (2 ml) and hexane (10 ml) were added. The organic layer was extracted and dried over MgSO$_4$. After filtering the liquid mixture, the solvent was distilled off under a reduced pressure to obtain an oily product. The resultant oily product was dissolved in Et$_2$O (5 ml) and cooled to 0° C. I$_2$ (800 mg, 3.15 mmol) was added to the liquid mixture and, after stirring for 30 min, an aqueous saturated solution of Na$_2$S$_2$O$_3$ (5 ml) was added, the organic layer was extracted with hexane (10 ml×2) and then washed with aqueous 1N solution of NaOH (5 ml). The resultant liquid mixture was dried over MgSO$_4$, filtered and then the solvent was distilled off under a reduced pressure. The obtained crude product was purified on silica gel chromatography to obtain the compound (41) (355 mg, 1.21 mmol, 85%).

$^1$H NMR (CCl$_4$, TMS)δ 0.89 (t, 3H, J=6Hz), 1.1–1.7 (m, cH), 1.90–2.45 (m, 2H), 2.28 (dt, 2H, J=6Hz, 2Hz.) 3.10 (brs. 1H, OH) 4.05 (dt, 1H, J=5Hz, 6Hz) 5.39 (d, 1H, J=1.5Hz), 6.55 (dd, 1H, J=5Hz, 15Hz).

IR (neat) 3340, 1605, 1250, 1030, 840 cm$^{-1}$.

$[α]^{25}_C$ −5.5° (c=1.45, CHCl$_3$).

Under an argon atmosphere, a solution of the compound (42) (75.0 g, 0.123 mmol) in THF (150 ml) was cooled to −78° C. and, after dropping n-BuLi (77 ml, 0.123 mmol; 1.6 M in hexane) thereto, stirred for 2 hours. The solution was slowly dropped to a solution of the compound (43) (16.9 g, 0.13 mmol) in THF (100 ml) cooled to −78° C. After stirring for one hour, an aqueous saturated solution of NH$_4$Cl (100 ml) was added to the reaction solution and extracted with hexane/Et$_2$O (200 ml×3). After drying the organic layer on MgSO$_4$ and filtration, the solvent was distilled off under a reduced pressure. The resultant crude product was purified on silica gel chromatography to obtain the compound (44) (19.7 g, 36%).

$^1$H NMR (CCl$_4$, TMS)δ 0.75–1.03 (m, 15H), 1.07–1.95 (m, 16H), 2.24 (t, 2H, J=7Hz), 2.98 (brs, 1H, OH), 3.56 (S, 3H), 3.82–4.07 (m, 1H), 5.55–6.43 (m, 2H).

EXAMPLE 25

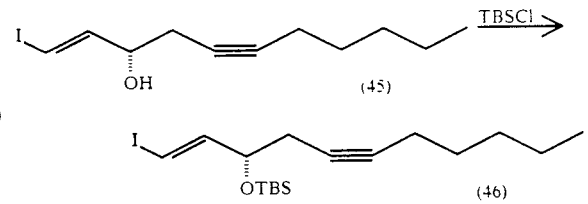

Imidazole (160 mg, 2.4 mmol) and TBSCl (260 mg, 1.72 mmol) were added to a solution of the compound (45) (355 mg, 1.21 mmol) in DMF (2 ml) and stirred at room temperature for 2 hours. Hexane (10 ml) and an aqueous saturated solution of NaHCO$_3$ (5 ml) were added to the liquid mixture and, after the organic layer was extracted, dried over MgSO$_4$. The resultant composition was purified on silica gel chromatography to obtain the compound (46) (478 mg, 1.18 mmol, 98%).

$^1$H NMR (CCl$_4$, PhH) 0.05 (S, 6H), 0.73–1.0 (m, 12H), 1.10–1.65 (m, 6H), 1.32–2.94 (m, 4H), 2.06 (q, 1H, 6Hz), 6.16 (d, 1H, J=15Hz), 6.53 (dd, 1H, J=5Hz, 15Hz).

$[α]^{25}_D$ +22.3° (c=1.52, CHCl$_3$).

EXAMPLE 26

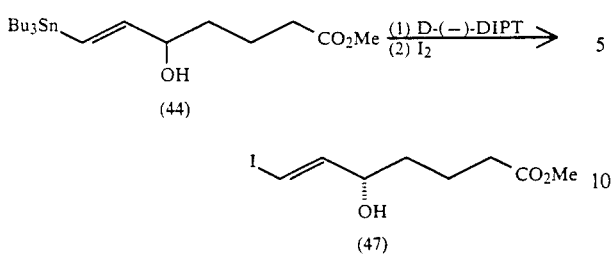

Under an argon atmosphere, a liquid mixture of Ti-(OiPr)$_r$ (0.48 ml, 1.61 mmol), molecular sieve (1 g) and CH$_2$Cl$_2$ (7 ml) was cooled to −20° C. and, after adding D-(−)-DIPT (0.40 ml, 1.90 mmol) thereto, stirred for 20 min. Subsequently, a solution of the compound (44) (3.00 g, 6.7 mmol) in CH$_2$Cl$_2$ (3 ml) was added, to which a solution of TBHP (3.5 ml, 10.05 mmol, 2.87 M in CH$_2$Cl$_2$) was dropped. After stirring for 36 hours, Me$_2$S (2 ml), an aqueous 10% solution of tartaric acid (1 ml), Et$_2$O (20 ml), NaF (1 g) and celite (1 g) were added and stirred at room temperature for one hour. The solvent was distilled off under a reduced pressure and the resultant crude product was dissolved in Et$_2$O (20 ml) and, after cooling to 0° C., I$_2$ (1.2 g, 4.7 mmol) was added. After stirring for 10 min, an aqueous saturated solution of Na$_2$S$_2$O$_3$ (10 ml) was added and extracted with Et$_2$O 920 ml×2). After drying organic layer on MgSO$_4$ and filtration, the solvent was distilled off under a reduced pressure. The resultant crude product was purified on silica gel chromatography to obtain the compound (47) (b 0.856 g, 45.0%).

$^1$H NMR (CCl$_4$, TMS)δ 2.15-2.90 (m, 4H), 2.27 (t, 2H, J=6Hz), 3.56 (S, 3H), 3.76 (brs, 1H), 3.88-4.16 (m, 1H), 6.24 (d, 1H, J=14Hz) 6.52 (dd, 1H, 5Hz, 14Hz).

IR (neat) 3340, 1720, 1605, 945 cm$^{-1}$.

$[\alpha]^{25}_D$+5.17° (c=1.70, CHCl$_3$).

EXAMPLE 27

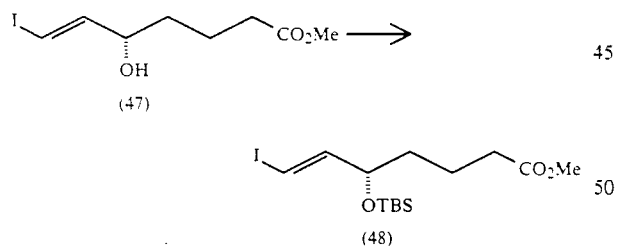

Imidazole (523 mg, 7/68 mmol) and TBSCl (8.68 mg, 5.76 mmol) was added to a liquid mixture of the compound (47) (1.01 g, 3.84 mmol) and DMF (10 ml) and stirred at room temperature for one hour. After cooling to 0° C., an aqueous solution of NaHCO$_3$ (10 ml) was added and extracted with hexane (20 ml×2). After drying the organic layer over MgSO$_4$, the resultant crude product was purified on silica gel chromatography to obtain the compound (48) (b 1.49 g, 98%).

$^1$H NMR (CDCl$_3$, δ0.00, (s, 3H) 0.02 (S, 3H, SiCH$_3$) 0.86 (m, 12H), 1.35-1.90 (m, 4H) 2.31 (t, 3H, J= 6Hz), 3.64 (S, 3H), 4.07 (q, 1H, J=5.5Hz), 6.17(dd, 1H, J=15Hz, 0.7Hz) 6.50 (dd, 1H, J=14Hz, 5.5Hz).

$^{13}$C NMR (CDCl$_3$) δ 173.4, 148.7, 75.9, 74.7, 51,2, 36.8, 33.8, 25.8, 20.2, −4.5, −4.9.

IR (neat) 1740, 1605, 1245, 1180, 940, 835 cm$^{-1}$.
$[\alpha]^{25}_D$−27.8° (c=2.73, CHCl$_3$).

EXAMPLE 28

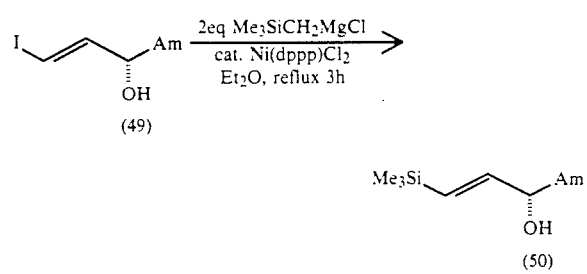

A solution of Me$_3$SiCH$_2$MgCl (148 mmol, 1.50 M in Et$_2$O) 98.4 ml) was dropped to a solution of the compound (49) (31.3 g, 123 mmol) in Et$_2$O (60 ml) cooled to 0° C. After stirring the mixture at room temperature for 5 min Ni(dppp)Cl$_2$ (667 mg, 1.23 mmol) was added and refluxed for 3 hours. After cooling to the room temperature, an aqueous saturated solution of NH$_4$Cl (150 ml) was added. After separating the organic layer, the aqueous layer was extracted with Et$_2$O (3×100 ml). After drying the resultant organic layer on MgSO$_4$, the solvent was distilled off under a reduced pressure. The resultant crude product 2 was purified on silica gel chromatography to obtain the compound (50) (26.3 g, 100%) as a transparent oily product.

$^1$H NMR (CCl$_4$) δ 0.04 (S, 9H), 0.09 (t, J=5.4Hz, 3H), 108-1.60 (m, 10H), 2.85 (brs, 1H), 3.72-4.00 (m, 1H), 5.17 (dd, J=7.0Hz, 16.6Hz, 1H), 5.49 (dt, J= 8.4Hz, 16.6Hz, 1H).

$^{13}$C NMR (CDCl$_3$) δ 131.9, 128.6, 73.6, 37.5, 31.9, 25.3, 22.8, 22.6, 14.0, −2.0.

IR (neat) 3320, 1660, 1250, 850 (cm$^{-1}$).
$[\alpha]^{25}_D$−23.3° (c=(0.92, CHCl$_3$).

What is claimed is:

1. An allyl alcohol derivative represented by following general formula (I), (II), (III) or (IV):

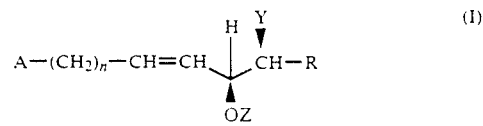

(I)

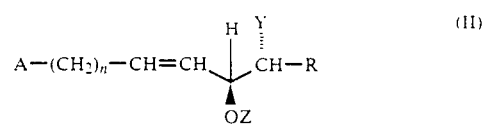

(II)

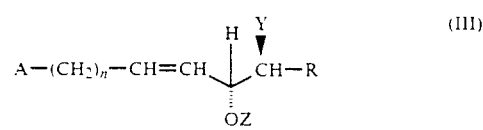

(III)

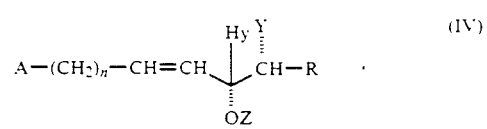

(IV)

wherein A represents R$^1$R$^2$R$^3$Sn, R$^1$R$^2$R$^3$ Si, halogen atom, —C≡CH or —C≡CSiR$^1$R$^2$R$^3$, in which R$^1$, R$^2$ and R$^3$ each represents an alkyl group having 1 to 5 carbon atoms, Y represents H or OZ', Z and Z' each represents H or a protection group for a hydroxyl group selected from the group consisting of trimethylsilyl group, t-butyldimethylsilyl group, phenyldimethylsilyl group, methoxymethyl group, ethoxyethyl group, tetrahydropyranyl group, benzyloxymethyl group, trityl group, acetyl group, p-nitrobenzoyl group and 2,4-dinitrophenylcarbonyl group, R represents an alkyl group having 1 to 10 carbon atoms, a $C_1$-$C_5$ alkoxyl carbonyl-substituted alkyl group having 1 to 10 carbon atoms, a bis($C_1$-$C_4$ alkoxy)methyl group-substituted alkyl group having 1 to 10 carbon atoms, a carboxyl-substituted alkyl group having 1 to 10 carbon atoms, an alkenyl group having 2 to 10 carbon atoms, a $C_1$-$C_5$ alkoxy carbonyl group-substituted alkenyl group having 2 to 10 carbon atoms, a carboxyl-substituted alkenyl group having 2 to 10 carbon atoms, a bis($C_1$-$C_4$ alkoxy)methyl group-substituted alkenyl group having 2 to 10 carbon atoms, an alkynyl group having 2 to 10 carbon atoms, a $C_1$-$C_5$ alkoxy carbonyl group-substituted alkynyl group having 2 to 10 carbon atoms, a carboxyl group-substituted alkynyl group having 2 to 10 carbon atoms or a bis($C_1$-$C_4$ alkoxy)methyl group-substituted alkynyl group having 2 to 10 carbon atoms, and n is 0 or 1, provided that A is not $R^1R^2R^3Si$ when R represents an alkyl group having 1 to 10 carbon atoms and Y represents H, provided that A is not $R^1R^2R^3Sn$ or $-C\equiv CH$ when R represents an alkyl group having 1 to 10 carbon atoms or a $C_1$-$C_5$ alkoxy carbonyl-substituted alkyl group having 1 to 10 carbon atoms and Y represents H, provided that A is not $-C\equiv C-SiR^1R^2R^3$ when R represents a $C_1$-$C_6$ alkoxy carbonyl-substituted alkyl group having 1 to 10 carbon atoms or a bis($C_1$-$C_4$ alkoxy)methyl group-substituted alkyl group having 1 to 10 carbon atoms and Y represents H, and provided that A is not halogen atom when R represents an alkyl group having 1 to 10 carbon atoms, an alkenyl group having 1 to 10 carbon atoms or a $C_1$-$C_5$ alkoxy carbonyl-substituted alkyl group having 1 to 10 carbon atoms and Y represents H.

2. A trans-halogen-substituted allyl alcohol derivative represented by general formula (V) or (VI):

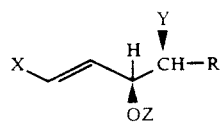

(V)

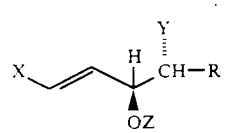

(VI)

wherein X represents a halogen atom, and Y, Z and R have the same meaning as defined in claim 1, provided that R is not an alkyl group having 1 to 10 carbon atoms, an alkenyl group having 1 to 10 carbon atoms or a $C_1$-$C_5$ alkoxy carbonyl-substituted alkyl group having 1 to 10 carbon atoms when Y represents H.

3. A cis-acetylene-substituted allyl alcohol derivative represented by general formula (VII) or (VIII):

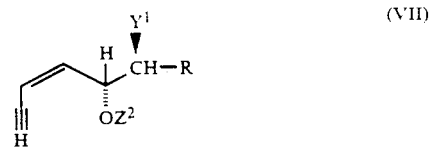

(VII)

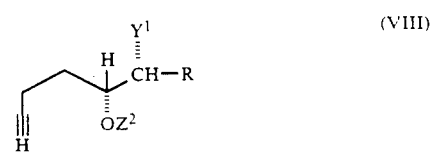

(VIII)

wherein $Z^2$ represents a hydrogen atom or a protection group for a hydroxyl group selected from the group consisting of trimethylsilyl group, t-butyldimethylsilyl group, phenyldimethylsilyl group, methoxymethyl group, ethoxyethyl group, tetrahydropyranyl group, benzyloxymethyl group, trityl group, acetyl group, p-nitrobenzoyl group and 2,4-dinitrophenylcarbonyl group, $Y^1$ represents a hydrogen atom or $OZ^3$, in which $Z^3$ represents a protection group for a hydroxyl group selected from the group consisting of trimethylsilyl group, t-butyldimethylsilyl group, phenyldimethylsilyl group, methoxymethyl group, ethoxyethyl group, tetrahydropyranyl group, benzyloxymethyl group, trityl group, acetyl group, p-nitrobenzoyl group and 2,4-dinitrophenylcarbonyl group, and R represents an alkyl group having 1 to 10 carbon atoms, a $C_1$-$C_5$ alkoxy carbonyl-substituted alkyl group with 1 to 10 carbon atoms, a bis($C_1$-$C_4$ alkoxy)methyl group-substituted alkyl group having 1 to 10 carbon atoms, a carboxy-substituted alkyl group having 1 to 10 carbon atoms, an alkenyl group having 2 to 10 carbon atoms, a $C_1$-$C_5$ alkoxy carbonyl group-substituted alkenyl group having 2 to 10 carbon atoms, a carboxyl-substituted alkenyl group having 2 to 10 carbon atoms, a bis($C_1$-$C_4$ alkoxy)methyl group-substituted alkenyl group having 2 to 10 carbon atoms, an alkynyl group having 2 to 10 carbon atoms, a $C_1$-$C_5$ alkoxy carbonyl group-substituted alkynyl group having 2 to 10 carbon atoms, a carboxyl group-substituted alkynyl group having 2 to 10 carbon atoms, or a bis($C_1$-$C_4$ alkoxy)methyl group-substituted alkynyl group having 2 to 10 carbon atoms, provided that R is not an alkyl group having 1 to 10 carbon atoms or a $C_1$-$C_5$ alkoxy carbonyl-substituted alkyl group having 1 to 10 carbon atoms when Y represents H.

* * * * *